United States Patent
Yoo et al.

(10) Patent No.: US 11,998,612 B2
(45) Date of Patent: Jun. 4, 2024

(54) METHOD FOR CONJUGATING ANTIBODY AND PHYSIOLOGICALLY ACTIVE SUBSTANCE

(71) Applicant: NOVELTY NOBILITY INC., Seongnam-si (KR)

(72) Inventors: Tae Hyeon Yoo, Yongin-si (KR); Jisoo Park, Suwon-si (KR); Yumi Lee, Suwon-si (KR)

(73) Assignee: NOVELTY NOBILITY INC., Seongnam-si (KR)

( * ) Notice: Subject to any disclaimer, the term of this patent is extended or adjusted under 35 U.S.C. 154(b) by 0 days.

(21) Appl. No.: 18/338,832

(22) Filed: Jun. 21, 2023

(65) Prior Publication Data
US 2024/0016947 A1 Jan. 18, 2024

Related U.S. Application Data

(62) Division of application No. 16/768,331, filed as application No. PCT/KR2018/014939 on Nov. 29, 2018, now Pat. No. 11,723,984.

(30) Foreign Application Priority Data

Nov. 29, 2017 (KR) .......................... 10-2017-0161452
Nov. 23, 2018 (KR) .......................... 10-2018-0146289

(51) Int. Cl.
- *A61K 47/68* (2017.01)
- *A61K 47/65* (2017.01)
- *C07K 7/08* (2006.01)

(52) U.S. Cl.
CPC .............. *A61K 47/68* (2017.08); *A61K 47/65* (2017.08); *C07K 7/08* (2013.01)

(58) Field of Classification Search
CPC ........ A61K 68/89; A61K 47/65; A61K 47/68; C07K 7/08
See application file for complete search history.

(56) References Cited

U.S. PATENT DOCUMENTS

| | | |
|---|---|---|
| 9,388,222 B2 | 7/2016 | Pastan et al. |
| 2004/0253247 A1 | 12/2004 | Dennis et al. |
| 2016/0041157 A1 | 2/2016 | Tsourkas et al. |

FOREIGN PATENT DOCUMENTS

| | | |
|---|---|---|
| JP | 2003-518075 A | 6/2003 |
| KR | 10-2009-0117406 A | 11/2009 |
| KR | 10-2014-0004530 A | 1/2014 |
| KR | 10-1695684 B1 | 1/2017 |
| WO | 2008/044038 A2 | 4/2008 |
| WO | 2014/145654 A1 | 9/2014 |

OTHER PUBLICATIONS

Yongwon Jung et al., "Photoactivable Antibody Binding Protein Site-Selective and Covalent Coupling of Antibody", Anal. Chem. 2009, pp. 936-942, vol. 81, No. 3.
Yoshihito Tanaka et al., "Photocrosslinkers illuminate interactions in living cells", Molecular BioSystems, 2008, pp. 473-480, vol. 4, No. 6.
Warren L. DeLano et al., "Convergent Solutions to Binding at a Protein-Protein Interface", Science, Feb. 18, 2000, pp. 1279-1283, vol. 287.
Jason W. Chin et al., "Addition of a photocrosslinking amino acid to the genetic code of *Escherichia coli*", Aug. 20, 2002, pp. 11020-11024, vol. 99, No. 17.
Byeong Sung Lee et al., "An efficient system for incorporation of unnatural amino acids in response to the four-base codon AGGA in *Escherichia coli*", Biochimica Biophysica Acta, S0304-4165, 2017.
Korean Office Action of KR 10-2018-0146289 dated Jul. 2, 2019.
International Search Report for PCT/KR2018/014939 dated May 21, 2019 [PCT/ISA/210].
Jisoo Park et al., "Peptide-Directed Photo-Cross-Linking for Site-Specific Conjugation of IgG", Bioconjugate Chemistry, 2018, vol. 29, pp. 3240-3244 (5 pages total).
Anna Konrad et al., "Covalent Immunoglobulin Labeling through a Photoactivable Synthetic Z Domain", Bioconjugate Chemistry, 2011, vol. 22, pp. 2395-2403 (9 pages total).
Extended European Search Report dated Jul. 16, 2021 in European Application No. 18882347.0.
Office Action dated Jun. 15, 2021 in Japanese Application No. 2020-549533.

*Primary Examiner* — James W Rogers
(74) *Attorney, Agent, or Firm* — Sughrue Mion, PLLC

(57) ABSTRACT

An antibody conjugating peptide including an amino acid having a photoreactive functional group, a physiologically active substance modified with the conjugating peptide, and an antibody conjugate having an antibody linked to the physiologically active substance are disclosed. When the physiologically active substance modified with the conjugating peptide is linked to the antibody, the conjugation efficiency between the antibody and the physiologically active substance is remarkably improved as compared to that of the conventional art, and thus the drug may be firmly bound without impairing the specificity of the antibody, thereby making it possible to accelerate commercialization of the antibody conjugate.

10 Claims, 16 Drawing Sheets

Specification includes a Sequence Listing.

☐: trastuzumab
△: PE24
○: trastuzumab-PE24.

(A) Her2-positive/trastuzumab-sensitive
(B) Her2-positive/trastuzumab-resistant
(C) Her2-positive/trastuzumab-resistant
(D) Her2-negative

SEQUENCE LISTING

```
Sequence total quantity: 29
SEQ ID NO: 1            moltype = AA  length = 13
FEATURE                 Location/Qualifiers
REGION                  1..13
                        note = FcIII
source                  1..13
                        mol_type = protein
                        organism = synthetic construct
SEQUENCE: 1
DCAWHLGELV WCT                                                    13
```

-continued

```
SEQ ID NO: 2              moltype = DNA  length = 39
FEATURE                   Location/Qualifiers
misc_feature              1..39
                          note = FcIII
source                    1..39
                          mol_type = other DNA
                          organism = synthetic construct
SEQUENCE: 2
gattgtgcat ggcatttagg tgaattagtg tggtgtaca                          39

SEQ ID NO: 3              moltype = AA  length = 241
FEATURE                   Location/Qualifiers
REGION                    1..241
                          note = beta-lactamase
source                    1..241
                          mol_type = protein
                          organism = synthetic construct
SEQUENCE: 3
ETLVKVKDAE DQLGARVGYI ELDLNSGKIL ESFRPEERFP MMSTFKVLLC GAVLSRIDAG    60
QEQLGRRIHY SQNDLVEYSP VTEKHLTDGM TVRELCSAAI TMSDNTAANL LLTTIGGPKE   120
LTAFLHNMGD HVTRLDRWEP ELNEAIPNDE RDTTMPAAMA TTLRKLLTGE LLTLASRQQL   180
IDWMEADKVA GPLLRSALPA GWFIADKSGA GERGSRGIIA ALGPDGKPSR IVVIYTTGSQ   240
A                                                                  241

SEQ ID NO: 4              moltype = DNA  length = 723
FEATURE                   Location/Qualifiers
misc_feature              1..723
                          note = beta-lactamase
source                    1..723
                          mol_type = other DNA
                          organism = synthetic construct
SEQUENCE: 4
gaaacgctgg tgaaagtaaa agatgctgaa gatcagttgg gtgcacgagt gggttacatc    60
gaactggaca tcaacagcgg taagatcctt gagagtttc gccccgaaga acgttttcca   120
atgatgagca ctttaaagt tctgctatgt ggcgcggtat tatcccgtat tgacgccggg   180
caagagcaac tcggtcgccg catacactat tctcagaatg acttggttga gtactcacca   240
gtcacagaaa agcatcttac ggatgggcatg acagtaagag aattatgcag tgctgccata   300
accatgagtg ataacactgc ggccaactta cttctgacaa cgatcggagg accgaaggag   360
ctaaccgctt ttttgcacaa catggggat catgtaactc gccttgatcg ttgggaaccg   420
gagctgaatg aagccatacc aaacgacgag cgtgacacca cgatgcctgc agcaatggca   480
acaacgttgc gcaaactatt aactggcgaa ctacttactc tagcttcccg gcaacaatta   540
atagactgga tggaggcgga taaagttgca ggaccacttc tgcgctcggc ccttccggct   600
ggctggttta tgctgataaa tctggagcc ggtgagcgtg gtctcgcgg tatcattgca   660
gcactgggc cagatggtaa gccctcccgt atcgtagtta tctacacgac ggggagtcag   720
gca                                                                723

SEQ ID NO: 5              moltype = AA  length = 452
FEATURE                   Location/Qualifiers
REGION                    1..452
                          note = beta-lactamase zymogen
source                    1..452
                          mol_type = protein
                          organism = synthetic construct
SEQUENCE: 5
GGAGVMTGAK FTQIQFGMTR QQVLDIAGAE NCETGGSFGD SIHCRGHAAG DYYAYATFGF    60
TSAAADAKVD SKSQEKLLAP SAPTLTLAKF NQVTVGMTRA QVLATVGQGS CTTWSEYYPA   120
YPSTAGVTLS LSCFDVDGYS STGAYRGSAH LWFTDGVLQG KRQWDLVSSG GGSGPLGVRG   180
GGSKLMDERN RQIAEIGASL IKHWGGGGGH PETLVKVKDA EDQLGARVGY IELDLNSGKI   240
LESFRPEERF PMMSTFKVLL CGAVLSRIDA GQEQLGRRIH YSQNDLVEYS PVTEKHLTDG   300
MTVRELCSAA ITMSDNTAAN LLLTTIGGPK ELTAFLHNMG DHVTRLDRWE PELNEAIPND   360
ERDTTTPVAM ATTLRKLLTG ELLTLASRQQ LIDWMEADKV AGPLLRSALP AGWFIADKSG   420
AGERGSRGII AALGPDGEPS RIVVIYTTGS QA                                 452

SEQ ID NO: 6              moltype = DNA  length = 1356
FEATURE                   Location/Qualifiers
misc_feature              1..1356
                          note = beta-lactamase zymogen
source                    1..1356
                          mol_type = other DNA
                          organism = synthetic construct
SEQUENCE: 6
ggcggtgcgg gggtgatgac cggggcgaag ttcacgcaga tccagttcgg gatgacacgt    60
cagcaggtcc tcgacatagc cggtgcgag aactgtgaga ccggcgggtc gttcgggac    120
agcatccact gccgggggca gcggcagg gactactacg cctacgccac cttcggcttc   180
accagcgccg ccgccgacgc gaaggtggac tcgaagagcc aggagaagct gctggccccg   240
agcgccccga cgctcaccct cgccaagttc aaccaggtca ccgtggggat gaccagggcc   300
caggtactgg cgaccgtcgg gcaggggtcc tgcaccacct ggagtgagta ctacccggcc   360
tatccgtcga cggccggggt gaccctcagc ctgtcctgct tcgatgtgga cggttactcg   420
tcgacggggg cctaccgagg ctcggcgcac ctctggttca ggacggggt gcttcagggc   480
```

```
aagcggcagt gggaccttgt aggatccggt ggcggcagcg gcccgctggg cgtgcgtggc    540
ggtggcagca agcttatgga cgagcgtaac cgtcaaattg cggaaatcgg cgcatctctg    600
atcaaaacact ggggtggcgg cggtggccac ccagaaacgc tggtgaaagt aaaagatgct    660
gaagatcagt tgggtgcacg agtgggttac atcgaactgg atctcaacag cggtaagatc    720
cttgagagtt ttcgcccccga agaacgtttt ccaatgatga gcacttttaa agttctgcta    780
tgtggcgcgg tattatcccg tattgacgcc gggcaagagc aactcggtcg ccgcatacac    840
tattctcaga atgacttggt tgagtactca ccagtcacag aaaagcatct tacgcgatggc    900
atgcagtaa gagaattatg cagtgctgcc ataaccatga gtgataacac tgcggccaac    960
ttacttctga caacgatcgg aggaccgaag gagctaaccg ctttttttgca caacatgggg   1020
gatcatgtaa ctcgccttga tcgttgggaa ccggagctga atgaagccat accaaacgac   1080
gagcgtgaca ccacgacgcc tgtagcaatg gcaacaacgt tgcgcaaact attaactggc   1140
gaactactta ctctagcttc ccggcaacaa ttgatagact ggatggaggc ggataaagtt   1200
gcaggaccac ttctgcgctc ggcccttccg gctggctggt tattgctga taaatctgga   1260
gccggtgagc gtggctctcg cggtatcatt gcagcactgg ggcagatgg tgagccctcc   1320
cgtatcgtag ttatctacac gacgggagt caggca                              1356

SEQ ID NO: 7              moltype = AA  length = 233
FEATURE                   Location/Qualifiers
REGION                    1..233
                          note = PE24
source                    1..233
                          mol_type = protein
                          organism = synthetic construct
SEQUENCE: 7
RHRQPRGWEQ LGGSPTGAEF LGDGGDVSFS TRGTQNWTVE RLLQAHAQLE ERGYVFVGYH     60
GTFLEAAQSI VFGGVAARSQ DLAAIWAGFY IAGDPALAYG YAQDQEPDAA GRIRNGALLR    120
VYVPASSLPG FYRTSLTLAA PEAAGEVERL IGHPLPLALD AITGPEEEGG RLETILGWPL    180
AERTVVIPSA IPTDPRNVGG DLDPSSIPDK EQAISALPDY ASQPGKPPRE DLK            233

SEQ ID NO: 8              moltype = DNA  length = 699
FEATURE                   Location/Qualifiers
misc_feature              1..699
                          note = PE24
source                    1..699
                          mol_type = other DNA
                          organism = synthetic construct
SEQUENCE: 8
cgtcatcgtc agccgcgtgg ttgggaacag cttggtggtt cgcccactgg tgctgaattt     60
ctcggtgatg gtggtgacgt tagctttagc actcggggaa cccagaattg gacagttgaa    120
cgtttactgc aagctcatgc acagctggaa gaacgtggtt atgttttttgt aggatatcat    180
ggtacattct tagaagcagc acaatctata gtttttcggtg gtgtcgctgc gcgttcgcag    240
gatctggcag caatttgggc aggttttctat atcgcaggag atcctgctct tgcatacggt    300
tacgcacagg atcaggaacc agatgcagct ggtagaatcc gaaatggagc attgcttaga    360
gtgtatgttc cggcatcatc tctgcccggt ttttatagga cgagtctgac acttgcagca    420
ccagaagcag caggcgaagt tgaacgctta attggtcatc cgctgcctct cgcactggac    480
gcaatcactg gtccggaaga agaaggtggt cggctgaaa cgatactagg atggccgtta    540
gctgagcgta ccgtggtaat tccatccgcc ataccaaccg atccacgtaa cgtaggtggt    600
gatttagacc cgagcagtat tcccgataaa gaacaggcaa tctcagcatt gccggactac    660
gcttcacaac tggtaaaacc tcctcgtgaa gatctgaag                             699

SEQ ID NO: 9              moltype = AA  length = 306
FEATURE                   Location/Qualifiers
REGION                    1..306
                          note = pBpa-aminoacyl tRNA synthetase
source                    1..306
                          mol_type = protein
                          organism = synthetic construct
SEQUENCE: 9
MDEFEMIKRN TSEIISEEEL REVLKKDEKS AGIGFEPSGK IHLGHYLQIK KMIDLQNAGF     60
DIIILLADLH AYLNQKGELD EIRKIGDYNK KVFEAMGLKA KYVYGSSFQL DKDYTLNVYR    120
LALKTTLKRA RRSMELIARE DENPKVAEVI YPIMQVNTSH YLGVDVAVGG MEQRKIHMLA    180
RELLPKKVVC IHNPVLTGLD GEGKMSSSKG NFIAVDDSPE EIRAKIKKAY CPAGVVEGNP    240
IMEIAKYFLE YPLTIKRPEK FGGDLTVNSY EELESLFKNK ELHPMRLKNA VAEELIKILE    300
PIRKRL                                                                306

SEQ ID NO: 10             moltype = DNA  length = 918
FEATURE                   Location/Qualifiers
misc_feature              1..918
                          note = pBpa-aminoacyl tRNA synthetase
source                    1..918
                          mol_type = other DNA
                          organism = synthetic construct
SEQUENCE: 10
atggacgagt tcgaaatgat taaacgcaac accagcgaaa ttatctctga agaagagctg     60
cgcgaggtgc tgaagaaaga cgagaagagc gcgggcattg ctttgagcc gtccggtaaa    120
attcacctgg tcactacct gcaaatcaag aagatgattg atctgcaaaa cgctggtttt    180
gacatcatta tcctgctggc ggacctgcac gcctacctga tcaaaagggcg agctggat    240
gagattcgca gatcggcga ctacaataag aaagtcttcg aagccatggg tttgaaggct    300
aaatacgtct acggtagcag cttttcagctg gataaggatt acacgttgaa tgtgtaccgt    360
```

```
ctggcgctga aaaccacgct gaaacgcgcc cgtcgttcca tggagctgat tgcgcgcgag    420
gatgagaatc caaaagttgc tgaggttatt taccctatta tgcaagttaa taccagccac    480
tacctgggtg ttgatgttgc cgtcggtggt atggagcaac gcaaaattca catgctggca    540
cgtgaactgc tgccgaaaaa ggttgtctgt attcataatc cggtcctgac cggcctggat    600
ggcgggggta aaatgagcag cagcaagggt aactttattg cagttgacga tagcccggaa    660
gaaatccgtg cgaagatcaa gaaagctac  tgcccggcag gcgtggttga gggtaacccg    720
atcatggaaa tcgccaagta ttttctggaa tacccactga cgattaagcg cccggagaaa    780
tttggcggcg acctgaccgt caacagctac gaggagctgg aaagcttgtt taagaacaaa    840
gaactgcatc cgatgcgcct gaaaaacgcc gtggcggaag agctgattaa gattctggaa    900
ccaattcgca aacgtctg                                                  918
```

```
SEQ ID NO: 11          moltype = AA   length = 12
FEATURE                Location/Qualifiers
REGION                 1..12
                       note = H5amber FcIII
source                 1..12
                       mol_type = protein
                       organism = synthetic construct
SEQUENCE: 11
DCAWLGELVW CT                                                        12

SEQ ID NO: 12          moltype = DNA   length = 39
FEATURE                Location/Qualifiers
misc_feature           1..39
                       note = H5amber FcIII
source                 1..39
                       mol_type = other DNA
                       organism = synthetic construct
SEQUENCE: 12
gattgtgcat ggtagttagg tgaattagtg tggtgtaca                            39

SEQ ID NO: 13          moltype = AA   length = 12
FEATURE                Location/Qualifiers
REGION                 1..12
                       note = V10amber FcIII
source                 1..12
                       mol_type = protein
                       organism = synthetic construct
SEQUENCE: 13
DCAWHLGELW CT                                                        12

SEQ ID NO: 14          moltype = DNA   length = 39
FEATURE                Location/Qualifiers
misc_feature           1..39
                       note = V10amber FcIII
source                 1..39
                       mol_type = other DNA
                       organism = synthetic construct
SEQUENCE: 14
gattgtgcat ggcatttagg tgaattatag tggtgtaca                            39

SEQ ID NO: 15          moltype = AA   length = 12
FEATURE                Location/Qualifiers
REGION                 1..12
                       note = W11amber FcIII
source                 1..12
                       mol_type = protein
                       organism = synthetic construct
SEQUENCE: 15
DCAWHLGELV CT                                                        12

SEQ ID NO: 16          moltype = DNA   length = 39
FEATURE                Location/Qualifiers
misc_feature           1..39
                       note = W11amber FcIII
source                 1..39
                       mol_type = other DNA
                       organism = synthetic construct
SEQUENCE: 16
gattgtgcat ggcatttagg tgaattagtg tagtgtaca                            39

SEQ ID NO: 17          moltype = AA   length = 271
FEATURE                Location/Qualifiers
REGION                 1..271
                       note = FcIII V10*-beta-lactamase
source                 1..271
                       mol_type = protein
                       organism = synthetic construct
```

```
SEQUENCE: 17
DCAWHLGELW CTGGEFGGGS GGGSGSGGGS ETLVKVKDAE DQLGARVGYI ELDLNSGKIL    60
ESFRPEERFP MMSTFKVLLC GAVLSRIDAG QEQLGRRIHY SQNDLVEYSP VTEKHLTDGM   120
TVRELCSAAI TMSDNTAANL LLTTIGGPKE LTAFLHNMGD HVTRLDRWEP ELNEAIPNDE   180
RDTTMPAAMA TTLRKLLTGE LLTLASRQQL IDWMEADKVA GPLLRSALPA GWFIADKSGA   240
GERGSRGIIA ALGPDGKPSR IVVIYTTGSQ A                                  271

SEQ ID NO: 18           moltype = DNA   length = 819
FEATURE                 Location/Qualifiers
misc_feature            1..819
                        note = FcIII V10*-beta-lactamase
source                  1..819
                        mol_type = other DNA
                        organism = synthetic construct
SEQUENCE: 18
gattgtgcat ggcatttagg tgaattatag tggtgtacag gtggtgaatt cggtggtggt    60
tcaggaggtg gttcaggatc cggcggtggc agcgaaacgc tggtgaaagt aaaagatgct   120
gaagatcagt tgggtgcacg agtgggttac atcgaactgg atctcaacag cggtaagatc   180
cttgagagtt tcgccccgga gaacgttttt ccaatgatga gcactttcaa agttctgcta   240
tgtggcgcgg tattatcccg tattgacgcc gggcaagagc aactcggtcg ccgcatacac   300
tattctcaga atgacttggt tgagtactca ccagtcacag aaaagcatct tacggatggc   360
atgacagtaa gagaattatg cagtgctgcc ataaccatag gtgataacac tgccgccaac   420
ttacttctga caacgatcgg aggaccgaag gagctaaccg ctttttttgca caacatgggg   480
gatcatgtaa ctcgccttga tcgttgggaa ccggagctga atgaagccat accaaacgac   540
gagcgtgaca ccacgatgcc tgcagcaatg caacaacgt tgcgcaaact attaactggc   600
gaactactta ctctagcttc ccggcaacaa ttaatagtag gcatggaggc ggataaagtt   660
gcaggaccac ttctgcgctc ggcccttccg gctggctggt ttattgctga taaatctgga   720
gccggtgagc gtgggtctcg cggtatcatt gcagcactgg ggccagatgg taagccctcc   780
cgtatcgtag ttatctacac gacggggagt caggcataa                          819

SEQ ID NO: 19           moltype = AA   length = 466
FEATURE                 Location/Qualifiers
REGION                  1..466
                        note = FcIII V10*-beta-lactamase zymogen
source                  1..466
                        mol_type = protein
                        organism = synthetic construct
SEQUENCE: 19
DCAWHLGELW CTPWGGMDER NRQIAEIGAS LIKHWGGGGG HPETLVKVKD AEDQLGARVG    60
YIELDLNSGK ILESFRPEER FPMMSTFKVL LCGAVLSRID AGQEQLGRRI HYSQNDLVEY   120
SPVTEKHLTD GMTVRELCSA AITMSDNTAA NLLLTTIGGP KELTAFLHNM GDHVTRLDRW   180
EPELNEAIPN DERDTTTPVA MATTLRKLLT GELLTLASRQ QLIDWMEADK VAGPLLRSAL   240
PAGWFIADKS GAGERGSRGI IAALGPDGEP SRIVVIYTTG SQAGSGGGSG PLGVRGGGSK   300
LAGVMTGAKF TQIQFGMTRQ QVLDIAGAEN CETGGSFGDS IHCRGHAAGD YYAYATFGFT   360
SAAADAKVDS KSQEKLLAPS APTLTLAKFN QVTVGMTRAQ VLATVGQQSC TTWSEYYPAY   420
PSTAGVTLSL SCFDVDGYSS TGFYRGSAHL WFTDGVLQGK RQWDLV                  466

SEQ ID NO: 20           moltype = DNA   length = 1404
FEATURE                 Location/Qualifiers
misc_feature            1..1404
                        note = FcIII V10*-beta-lactamase zymogen
source                  1..1404
                        mol_type = other DNA
                        organism = synthetic construct
SEQUENCE: 20
gattgtgcat ggcatttagg tgaattatag tggtgtacac catggggcgg tatggacgag    60
cgtaaccgtc aaattgcgga aatcggcgca tctctgatca aacactgggg tggcggcggt   120
ggccacccag aaacgctggt gaaagtaaaa gatgctgaag atcagttggg tgcacgagtg   180
ggtttacatcg aactggatct caacagcggt aagatccttg agagttttcg ccccgaagaa   240
cgttttccaa tgatgagcac ttttaaagtt ctgctatgtg gcgcggtatt atcccgtatt   300
gacgccgggc aagagcaact cggtcgccgc atacactatt ctcagaatga cttggttgag   360
tactcaccag tcacagaaaa gcatcttacg gatggcatga cagtaagaga attatgcagt   420
gctgccataa ccatggagtga taacactgcg gccaacttac ttctgacaac gatcggagga   480
ccgaaggagc taaccgcttt tttgcacaac atggggatg atcataactcg ccttgatcgt   540
tgggaaccgg agctgaatga agccatacca aacgacgagc gtgacaccac gacgcctgta   600
gcaatggcaa caacgttgcg caaactatta actggcgaac tacttactct agcttcccgg   660
caacaattga tagactggat ggaggcggat aaagttgcag gaccacttct gcgctcggcc   720
cttccggctg gctggtttat tgctgataaa tctggagccg gtgagcgtgg gtctcgcggt   780
atcattgcag ctgggggcc agatggtgag ccctcccgta tcgtagttat ctacacgcgt   840
gggagtcagg caggatccgg tggcggcagc ggcccgctgg gcgtgcgtgg cggtggcagc   900
aagcttgcgg gggtgatgac cggggcgaag ttcacgcaga tccagttcgg gatgacacgt   960
cagcaggtcc tcgacatagc cggtgcgag aactgtgaga ccggcgggtc gttcggggac  1020
agcatccact gccgggggca cgcggcaggg gactactacg cctacgccac cttcggcttc  1080
accgccgcag ccgccgacgc gaaggtgac tcgaagagc aggagaagct gctgcccccg  1140
agcgccccga cgctcaccct gccaagttc aaccaggtca ccgtgggat gaccagggcg  1200
caggtactgg cgaccgtcgg gcaggggtcc tgcaccacct ggagtgagta ctacccggcc  1260
tatccgtcga cggccggggt gaccctcagc ctgtcctgct cgatgtggga cggttactcg  1320
tcgacggggt ctctaccgag gtcggcgcac tctggttcca ggacgggtt gcttcaggc  1380
aagcggcagt gggaccttgt ataa                                         1404
```

```
SEQ ID NO: 21           moltype = AA  length = 259
FEATURE                 Location/Qualifiers
REGION                  1..259
                        note = FcIII V10*-PE24
source                  1..259
                        mol_type = protein
                        organism = synthetic construct
SEQUENCE: 21
DCAWHLGELW CTGGEFGGGS GGGSGSRHRQ PRGWEQLGGS PTGAEFLGDG GDVSFSTRGT    60
QNWTVERLLQ AHAQLEERGY VFVGYHGTFL EAAQSIVFGG VAARSQDLAA IWAGFYIAGD   120
PALAYGYAQD QEPDAAGRIR NGALLRVYVP ASSLPGFYRT SLTLAAPEAA GEVERLIGHP   180
LPLALDAITG PEEEGGRLET ILGWPLAERT VVIPSAIPTD PRNVGGDLDP SSIPDKEQAI   240
SALPDYASQP GKPPREDLK                                                259

SEQ ID NO: 22           moltype = DNA  length = 929
FEATURE                 Location/Qualifiers
misc_feature            1..929
                        note = FcIII V10*-PE24
source                  1..929
                        mol_type = other DNA
                        organism = synthetic construct
SEQUENCE: 22
catatgaaaa aaaccgcaat tgcgattgca gttgcattgg ctggttttgc aacggtggca    60
caagcagcta gccatcatca tcaccatcac ggcagtttag ttccgcgtgg cagcggtggt   120
ggaagtaagc ttggaggtga ttgtgcatgg catttaggtg aattatagtg gtgtacaggt   180
ggtgaattcg gtggtggttc aggaggtggt tcaggatccc gtcatcgtca gccgcgtggt   240
tgggaacagc ttggtggttc gcccactggt gctgaatttc tcggtgatgg tggtgacgtt   300
agctttagca ctcggggaac ccagaattgg acagttgaac gtttactgca agctcatgca   360
cagctggaag aacgtggtta tgttttttgta ggatatcatg gtacattctt agaagcagca   420
caatctatag ttttcggtgg tgtcgctgcg cgttcgcagg atctggcagc aatttgggca   480
ggtttctata tcgcaggaga tcctgctctt gcatacggtt acgcacagga tcaggaacca   540
gatgcagctg gtagaatccg aaatggagca ttgcttagag tgtatgttcc ggcatcatct   600
ctgcccggtt tttataggac gagtctgaca cttgcagcac cagaagcagc aggcgaagtt   660
gaacgcttaa ttggtcatcc gctgcctctc gcactgacg caatcactgg tccggaagaa   720
gaaggtggtc ggctgaaaac gatactagga tggccgttag ctgagcgtac cgtggtaatt   780
ccatccgcca taccaaccga tccacgtaac gtaggtggtg atttagaccc gagcagtatt   840
cccgataaag aacaggcaat ctcagcattg ccggactacg cttcacaacc tggtaaacct   900
cctcgtgaag atctgaagta agcggccgc                                     929

SEQ ID NO: 23           moltype = RNA  length = 77
FEATURE                 Location/Qualifiers
misc_feature            1..77
                        note = tRNACUA
source                  1..77
                        mol_type = other RNA
                        organism = synthetic construct
SEQUENCE: 23
cccgccttag ttcagcaggg cagaacggcg gactctaaat ccgcatggca cgggttcaaa    60
tcccgtaggc gggacca                                                   77

SEQ ID NO: 24           moltype = DNA  length = 49
FEATURE                 Location/Qualifiers
misc_feature            1..49
                        note = BamhI- -f primer
source                  1..49
                        mol_type = other DNA
                        organism = synthetic construct
SEQUENCE: 24
aaccttggat ccggcggtgg cagcgaaacg ctggtgaaag taaagatg                 49

SEQ ID NO: 25           moltype = DNA  length = 39
FEATURE                 Location/Qualifiers
misc_feature            1..39
                        note = TEM1-NotI-r primer
source                  1..39
                        mol_type = other DNA
                        organism = synthetic construct
SEQUENCE: 25
aaggttgcgg ccgctttatt accaatgctt aatcagtga                           39

SEQ ID NO: 26           moltype = DNA  length = 34
FEATURE                 Location/Qualifiers
misc_feature            1..34
                        note = NdeI-FcIII V10*-f primer
source                  1..34
                        mol_type = other DNA
                        organism = synthetic construct
```

```
SEQUENCE: 26
aaccttcata tgaagaaaac agcaattgct attg                                      34

SEQ ID NO: 27           moltype = DNA  length = 33
FEATURE                 Location/Qualifiers
misc_feature            1..33
                        note = FcIII V10*-NcoI -r primer
source                  1..33
                        mol_type = other DNA
                        organism = synthetic construct
SEQUENCE: 27
aaggttccat ggtgtacacc actataattc acc                                       33

SEQ ID NO: 28           moltype = DNA  length = 40
FEATURE                 Location/Qualifiers
misc_feature            1..40
                        note = NcoI -beta-lactamase zymogen -f primer
source                  1..40
                        mol_type = other DNA
                        organism = synthetic construct
SEQUENCE: 28
aaccttccat ggggcggtat ggacgagcgt aaccgtcaaa                                40

SEQ ID NO: 29           moltype = DNA  length = 40
FEATURE                 Location/Qualifiers
misc_feature            1..40
                        note = beta-lactamase zymogen-NotI-r primer
source                  1..40
                        mol_type = other DNA
                        organism = synthetic construct
SEQUENCE: 29
aaggttgcgg ccgctttata caaggtccca ctgccgcttg                                40
```

METHOD FOR CONJUGATING ANTIBODY AND PHYSIOLOGICALLY ACTIVE SUBSTANCE

CROSS REFERENCE TO RELATED APPLICATIONS

This application is Divisional of U.S. application Ser. No. 16/768,331 filed May 29, 2020, which is a National Stage of International Application No. PCT/KR2018/014939 filed Nov. 29, 2018, claiming priority based on Korean Patent Application No. 10-2017-0161452 filed Nov. 29, 2017 and Korean Patent Application No. 10-2018-0146289 filed Nov. 23, 2018.

INCORPORATION BY REFERENCE OF SEQUENCE LISTING

The content of the electronically submitted sequence listing, file name: Q288905_Sequence Listing_as_Filed.XML; size: 46,520 bytes; and date of creation: Jun. 21, 2023, filed herewith, is incorporated herein by reference in its entirety.

TECHNICAL FIELD

The present invention relates to an Fc site-specific conjugating peptide in which position 5, 10, or 11 of an Fc binding peptide represented by an amino acid sequence of SEQ ID NO: 1 is substituted with an amino acid having a photoreactive functional group, a physiologically active substance modified with the conjugating peptide, an antibody conjugate in which an antibody is covalently linked to the physiologically active substance modified with the conjugating peptide, and a method of producing the antibody conjugate.

BACKGROUND ART

For the past 20 years, antibody engineering has advanced thanks to the development of techniques for producing chimeric antibodies (chimeric mAbs), humanized antibodies (humanized mAb), and fully human antibodies (fully human mAbs) on the basis of hybridoma technology for developing monoclonal antibodies (mAbs) in mice, and antibodies are now recognized as a therapeutic drug (therapeutic mAb). 28 types of therapeutic antibodies have been approved by the FDA to date, and are used as agents for treating a wide range of diseases, such as transplant rejection, cancer, autoimmune diseases, inflammation, heart disease, and infection, and about 300 therapeutic antibodies are currently in the clinical development stage, with more therapeutic antibodies expected to be developed and commercialized in the future. In addition, many studies are ongoing to develop next-generation therapeutic antibodies that have improved efficacy over conventional antibodies (naked mAb). Among these, conjugates, in which a monoclonal antibody having a binding affinity to a specific antigen and a substance having biological activity are linked, are actively researched. When these antibody conjugates are developed as therapeutic drugs, the high efficacy and reduced side effects of the substance can be expected due to the target specificity of antibodies, and moreover, the characteristics of antibodies, such as no in-vivo toxicity, low immunogenicity, and long in-vivo half-life, are also factors that can accelerate the commercialization of developed antibody conjugate drugs. Antibody-drug conjugates (ADCs), in which an antibody and a small molecule drug exhibiting cytotoxicity are linked, have already been developed by pharmaceutical firms and are used as tumor-targeting therapeutic agents.

For development as a therapeutic drug, an antibody conjugate should retain the properties of an unconjugated antibody and the biologically active substance. The antibody conjugate must be able to maintain the same affinity as that of the (naked) antibody without conjugation to the substance. That is, natural antigen-antibody binding should not be hindered by linking an antibody with a substance. In addition, the substance in the antibody conjugate should also be able to exhibit activity after reaching a target. That is, in the antibody conjugate, the respective intrinsic properties of the monoclonal antibody and the biologically active substance must be maintained, which is determined by a method of conjugating the two molecules. In addition, linkers used for conjugation must be stable in the blood to prevent the substance from being separated from the antibody and to reach target tissues/cells. In general, linkers used in antibody conjugates are an acid-labile hydrazone, a protease-cleavable peptide, and a disulfide that is susceptible to a reducing agent. Non-cleavable thioether linkers are also used. For the conjugation of an antibody and a substance, a method using a reactive group (an ε-amino group of lysine or a thiol group of cysteine) of an antibody, or a method in which a cysteine residue is introduced into an antibody by a mutation and which uses the reactivity of the thiol group is generally used. The method using a functional group of an antibody itself cannot specify the position where a substance is linked, and the molar ratio of the antibody to the substance is not controllable, thus creating a heterogeneous antibody conjugate. In the case of using the thiol group of cysteine artificially introduced into an antibody, it is necessary to mutate the antibody, and it is difficult to predict the effect on the structure and activity of the antibody itself.

Recently, a method of producing a low-molecular-weight Fc conjugating peptides by introducing a photoreactive artificial amino acid into Fc binding peptides and then producing an antibody-drug conjugate using a drug modified with the Fc conjugating peptide (Korean Patent Publication No. 10-2014-0004530 (2014 Jan. 13)) have been reported. However, the peptide material used in the above inventions must be prepared through chemical synthesis, and thus, the conjugation method is limited to the case of conjugating a drug to an antibody, and it is difficult to use for the conjugation of a substance such as a protein and an antibody. In addition, the non-specific reactivity of the photoreactive amino acid (experimental example: using photo-leucine, photo-methionine) used in the above inventions makes it difficult to develop antibody conjugates as pharmaceuticals (Yoshihito Tanaka et al, *Molecular BioSystems*, 4(6):473-480, 2008).

Therefore, the inventors of the present invention developed an Fc site-specific conjugating peptide in which a site of an Fc binding peptide, which is capable of binding the Fc domain of an antibody, is substituted with an amino acid having a photoreactive functional group (para-benzoyl phenylalanine(pBpa)), and prepared a physiologically active substance modified with the conjugating peptide, and as a result of covalently linking the antibody and the substance through a reaction based on the introduced photoreactive amino acid, confirmed that the substance is conjugated to the antibody in a site-specific manner and with a high efficiency, thus completing the present invention.

The above information described in the Background Art section is provided only for the purpose of improving understanding of the background of the present invention, and thus may not include information that is already known to those of ordinary skill in the art to which the present invention pertains.

DISCLOSURE

Technical Problem

It is an object of the present invention to provide a peptide capable of site-specifically conjugating an antibody and a substance through photoreaction.

It is another object of the present invention to provide a substance modified with the peptide.

It is a further object of the present invention to provide a method of producing an antibody conjugate in which the substance modified with the peptide and an antibody are linked.

It is a further object of the present invention to provide an antibody conjugate produced using the production method.

Technical Solution

To achieve the above objects, the present invention provides an Fc site-specific conjugating peptide in which position 5, 10, or 11 in an Fc binding peptide represented by an amino acid sequence of SEQ ID NO: 1 is substituted with an amino acid having a photoreactive functional group.

The present invention also provides a substance modified with the conjugating peptide, wherein the substance is linked to the peptide either directly or via a linker.

The present invention also provides a method of producing an antibody conjugate, the method comprising: (a) mixing the substance modified with the conjugating peptide and an Fc domain-containing molecule; (b) irradiating the mixture with light to induce a photoreaction and then to produce an antibody conjugate in which the photoreactive functional group of the substance modified with the conjugating peptide and the Fc domain-containing molecule are covalently linked; and (c) obtaining the produced antibody conjugate.

The present invention also provides an antibody conjugate in which an antibody is linked to the substance modified with the conjugating peptide.

BRIEF DESCRIPTION OF DRAWINGS

FIG. 8 illustrates the results of.

DETAILED DESCRIPTION AND EXEMPLARY EMBODIMENTS

Unless defined otherwise, all technical and scientific terms used herein have the same meanings as those commonly understood by one of ordinary skill in the art to which the present invention pertains. In general, the nomenclature used herein and experimental methods described below are well known and commonly used in the art.

Figure 1:
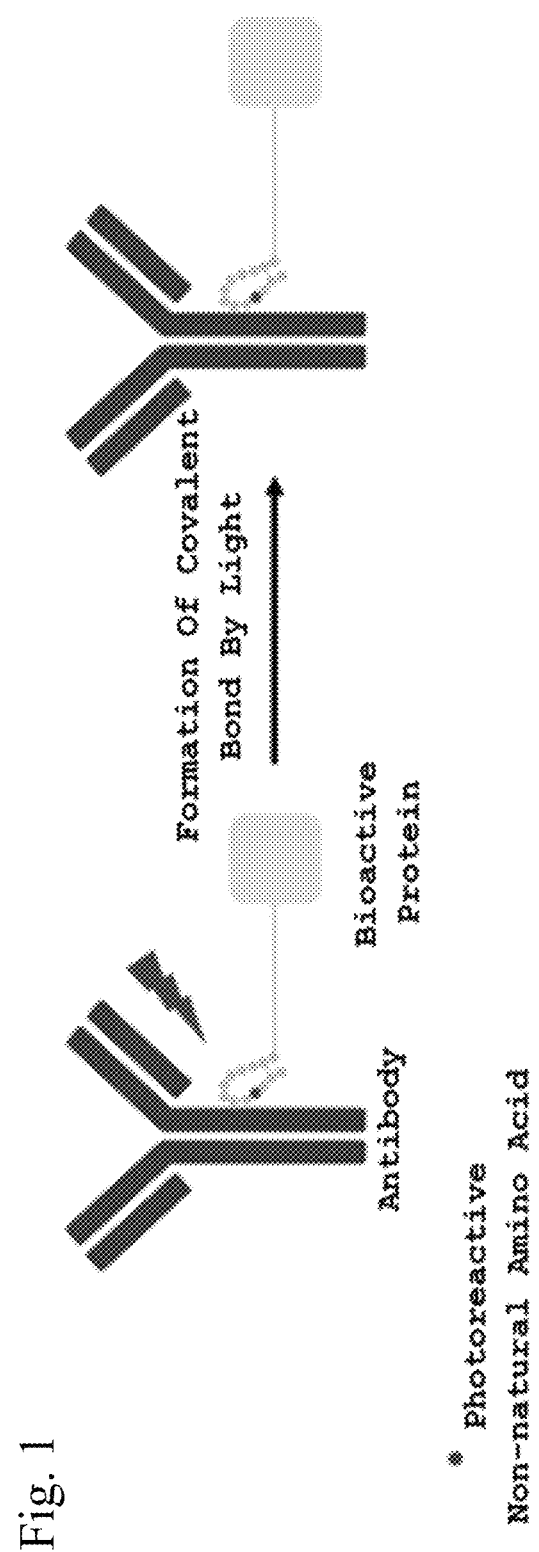
FIG. 1 is a scheme illustrating a technique for conjugation of an antibody and a substance according to the present invention.
Figure 2:
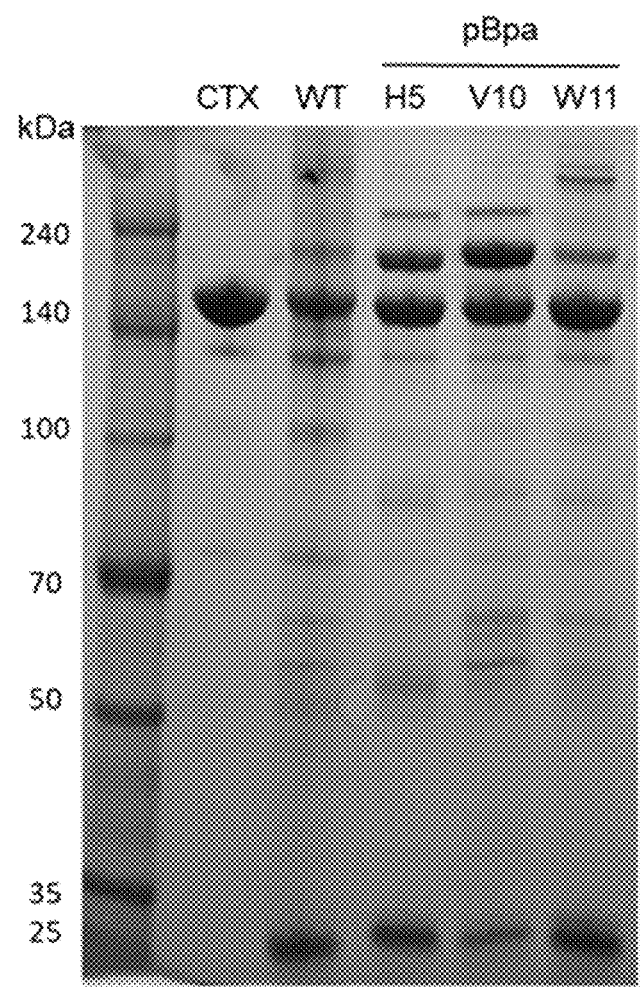
FIG. 2 illustrates electrophoresis results after a photoreaction between an antibody and a substance modified with a photoreactive peptide of the present invention in order to determine a substitution site of p-benzoyl phenylalanine in the Fc binding peptide (SEQ ID NO: 1).

In the present invention, as a result of covalently linking a substance modified with an Fc site-specific conjugating peptide in which position 5, 10, or 11 of an Fc binding peptide is substituted with an amino acid having a photoreactive functional group, to an antibody, it was confirmed that, unlike conventional antibody binding peptides, irreversible chemical bonds were formed, and the conjugation efficiency of the substance modified with the conjugating peptide to the antibody was enhanced depending on the introduction site of the photoreactive functional group (see FIG. 2).

Therefore, in one aspect, the present invention relates to an Fc site-specific conjugating peptide in which position 5, 10, or 11 in an Fc binding peptide represented by an amino acid sequence of SEQ ID NO: 1 is substituted with an amino acid having a photoreactive functional group.

In the present invention, the Fc binding peptide (amino acid sequence of SEQ ID NO: 1, gene sequence of SEQ ID NO: 2) is a short peptide consisting of 13 amino acids that site-specifically bind to the CH3-CH2 interface region of the Fc domain of a human-derived antibody (IgG1) (W. L. DeLano et al, *Science*, 2000). The peptide has a U-shaped structure because two cysteines form a disulfide bond.

In the present invention, the position of substitution with an amino acid having a photoreactive functional group may be position 10.

In the present invention, the Fc site-specific conjugating peptide substituted with an amino acid having a photoreactive functional group may be produced by identifying the amino acid sequence of an Fc binding peptide, expressing the peptide using a known method, for example, by constructing an expression vector capable of expressing the peptide, transforming the vector into a host cell, and expressing the peptide using a recombination technique, or may be produced by performing artificial synthesis, and then substituting at least one amino acid residue with an amino acid having a photoreactive functional group or introducing the same, or may be synthesized by including an amino acid having at least one photoreactive functional group in the artificial synthesis.

The introduction of the gene may be performed using a commonly known genetic manipulation method. For example, physical methods such as a method using a vector such as a virus, a non-viral method using a synthetic phospholipid or a synthetic cationic polymer, and an electric permeation method for introducing a gene by applying a temporary electrical stimulus to a cell membrane may be used, but the present invention is not limited thereto.

In the present invention, "amplification" conceptually encompasses mutation, substitution, or deletion of a certain base of the corresponding gene, introduction of a certain base, or introduction of a gene derived from another microorganism encoding the same enzyme to increase the activity of the corresponding enzyme.

In the present invention, "vector" means a DNA construct containing a DNA sequence operably linked to a suitable regulatory sequence capable of expressing DNA in a suitable host.

The vector may be a plasmid, a phage particle, or simply a potential genomic insert. Once the vector is transformed into a suitable host, the vector can replicate and function independently of the genome of the host, or in some cases, may be integrated with the genome itself. Since plasmids are currently the most commonly used form of vector, the terms "plasmid" and "vector" may be used interchangeably throughout the specification of the present invention. However, the present invention includes other forms of vectors having functions identical to those already known or yet to be known in the art.

In the present invention, "expression vector" commonly refers to a recombinant carrier, into which a fragment of heterologous DNA is inserted, and generally means a fragment of double-stranded DNA. Here, the heterologous DNA refers to exogenous DNA that is not naturally found in the host cell. Once an expression vector is present in a host cell, the expression vector can replicate independently of the host chromosomal DNA, and several copies of the vector and inserted (heterologous) DNA thereof may be produced. As is well known in the art, in order to increase the expression level of a transgene in a host cell, the gene must be operably linked to a transcriptional/translational expression regulatory sequence that functions in a selected expression host. Preferably, the expression regulatory sequence and the corresponding gene are included in one expression vector including a bacterial selection marker and a replication origin. When the expression host is a eukaryotic cell, the expression vector should further include a useful expression marker in the eukaryotic expression host.

In the present invention, "integrated vector" refers to a vector whose integration or insertion into a nucleic acid is performed via an integrase. Examples of integrated vectors include, but are not limited to, retroviral vector, and transposon- and adeno-related viral vectors.

Another embodiment of the present invention provides a host cell transformed or transfected with the vector. The term "transformation" as used herein means introducing DNA into a host and making the DNA replicable by an extrachromosomal factor or chromosomal integration. This includes any method of introducing a nucleic acid into an organism, cell, tissue or organ, and may be performed by selecting standard techniques suitable for the host cell, as is well known in the art. These methods include electroporation, protoplast fusion, calcium phosphate ($CaPO_4$) precipitation, calcium chloride ($CaCl_2$) precipitation, agitation with silicon carbide fibers, agrobacteria-mediated transformation, PEG, dextran sulfate, lipofectamine, and drying/inhibition-mediated transformation methods, but the present invention is not limited thereto. The host cell of the present invention may be a prokaryotic or eukaryotic cell. In addition, a host having high DNA introduction efficiency and high expression efficiency of the introduced DNA is usually used. Examples of the host cell that can be used include well-known eukaryotic and prokaryotic hosts such as *E. coli, Pseudomonas, Bacillus, Streptomyces*, fungi, and yeast, insect cells such as those of *Spodoptera frugiperda* (SF9), animal cells such as CHO and mouse cells, African green monkey cells such as COS 1, COS 7, BSC 1, BSC 40, and BMT 10, and tissue-cultured human cells.

Of course, it should be understood that not all vectors function identically in expressing the DNA sequences of the present invention. Similarly, not all hosts function identically for the same expression system. However, those skilled in the art will be able to make appropriate selection from among a variety of vectors, expression regulatory sequences, and hosts without excessive burden of experimentation and without departing from the scope of the present invention. For example, selection of a vector should be carried out in consideration of the host because the vector must replicate therein. The number of replications of the vector, the ability to control the number of replications, and the expression of other proteins encoded by the corresponding vector, such as the expression of antibiotic markers, should also be considered. In selecting the expression regulatory sequence, various factors need to be considered. For example, the relative strength of the sequence, possibility of regulation, and compatibility with the DNA sequence of the present invention should be considered, particularly in relation to possible secondary structures. A single-cell host may be selected in consideration of factors such as the selected vector, the toxicity of the product encoded by the DNA sequence according to the present invention, the secretion characteristics, the ability to accurately fold proteins, culture and fermentation factors, and ease of purification of the product encoded by the DNA sequence according to the present invention. Within the scope of these variables, those skilled in the art can select various vector/expression regulatory sequence/host combinations capable of expressing the DNA sequences of the present invention in fermentation or large-scale animal culture. As a screening method for cloning cDNA of NSP proteins through expression cloning, a binding method, a panning method, a film emulsion method, or the like may be applied.

In the present invention, "protoplast fusion" refers to a technique for removing the cell wall of a protoplast, such as plant cells or bacteria, and fusing two cells with different traits using the protoplast. For protoplast fusion, there are chemical methods such as adding a metal ion such as calcium or magnesium to a high concentration of an osmotic solution, or physical methods such as exposing a protoplast to an electric shock to temporarily create small pores in the cell membrane, thereby increasing DNA absorption of the protoplast.

In the present invention, the "photoreactive functional group" may be a functional group capable of absorbing light of a specific wavelength upon light irradiation to form a covalent bond with an adjacent reactive functional group.

When the Fc site-specific conjugating peptide having a photoreactive functional group according to the present invention, is mixed with an antibody, the conjugating peptide is located adjacent to or binds to the Fc domain of the antibody, due to its binding specificity which is an inherent property thereof. Thereafter, when the mixture is irradiated with light, the mixture may absorb light of a specific wavelength and thereby form a covalent bond, through the photoreactive functional group, with a residue having a group reactive toward the photoreaction on the Fc domain of the antibody, adjacent thereto. That is, the Fc site-specific conjugating peptide of the present invention may be covalently linked to a specific functional group of the Fc domain through the photoreactive functional group upon light irradiation.

In the present invention, the amino acid having a photoreactive functional group may be p-benzoyl phenylalanine. An artificial amino acid having a photoreactive functional group may comprise photo-leucine, photo-methionine, azidophenylalanine, or the like, but the photoreactive functional group used in the present invention preferentially acts on a specific functional group and has specificity in that covalent bonds are activated through light of a long wavelength, i.e., low light energy.

p-Benzoyl phenylalanine of the present invention is represented by Formula 1 below.

[Formula 1]

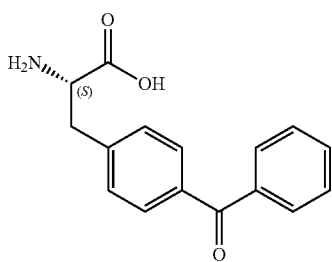

In another aspect, the present invention relates to a substance modified with a conjugating peptide wherein the substance is linked to the above-described peptide, either directly or via a linker.

In the present invention, the substance may be a therapeutic agent or a diagnostic agent, and the therapeutic or diagnostic agent may be selected from the group consisting of an enzyme, a hormone, a cytokine, an antibody, an antibody fragment, an analgesic, an antipyretic, an anti-inflammatory agent, an antibiotic, an anti-viral agent, an antifungal drug, a cardiovascular drug, a drug that acts on the central nervous system, a drug that affects renal function and electrolyte metabolism, and a chemotherapeutic agent.

The substance of the present invention may be a therapeutic agent or a diagnostic/detection agent. Particularly, the antibody used as the substance may be a therapeutic antibody. About 30 types of therapeutic antibodies are currently approved by the FDA, and the safety thereof is very high due to properties that are almost the same as those of IgG present in vivo. Antibodies are used as therapeutic agents for a wide range of disorders (e.g., transplant rejection, cancer, autoimmune diseases and inflammation, heart diseases, and infections). In particular, when an Fc domain-containing molecule is a therapeutic antibody, the therapeutic antibody recognizes and binds to a receptor protein or antigen protein specifically present in diseased tissues, and thus has very high specificity. Thus, when a molecular imaging probe or a drug carrier is combined as a substance with a therapeutic antibody, this may be converted into a theragnosis agent capable of monitoring a treatment process and a drug combination effect. In addition, by combining a molecular imaging probe or a drug delivery system with a simple targeting antibody, it is possible to develop a theragnosis agent for diagnosis, treatment, or simultaneous diagnosis and treatment.

Non-limiting examples of therapeutic agents include antibodies, antibody fragments, drugs, toxins, nucleases, hormones, immunomodulators, chelators, boron compounds, photoactive agents or dyes, and radioactive isotopes.

Non-limiting examples of diagnostic/detection agents include radioisotopes, dyes (e.g., biotin-streptavidin complex), contrast agents, fluorescent compounds or molecules, and enhancing agents (e.g., paramagnetic ions) for magnetic resonance imaging (MRI). Preferably, the diagnostic agent includes radioisotopes, enhancing agents for use in magnetic resonance imaging, and fluorescent compounds. To load an antibody component with radioactive metals or paramagnetic ions, it may be necessary to react the antibody component with a reagent having a long tail attached to a plurality of chelating groups for binding the ions. The tail may be a polymer such as polylysine or a polysaccharide, or a derivatized or derivatizable chain having pendant groups that can bind to chelating groups such as ethylenediaminetetraacetic acid (EDTA), diethylenetriaminepentaacetic acid (DTPA), porphyrin, polyamine, crown ether, bis-thiosemicarbazone, and polyoximes, and that is known to be useful for the above purpose. A chelate may be normally linked to the Fc site-specific conjugating peptide by a functional group which enables the formation of a bond to the molecule with minimal loss of immunoreactivity and minimal aggregation, and/or via internal crosslinking.

In particular, useful metal-chelate combinations include diagnostic isotopes, 2-benzyl-DTPA, and monomethyl and cyclohexyl analogs thereof used in a general energy range of 60 keV to 4,000 keV, and examples of radioactive imaging agents include $^{125}$I, $^{131}$I, $^{123}$I, $^{124}$I, $^{62}$Cu, $^{64}$Cu, $^{18}$F, $^{111}$In, $^{67}$Ga, $^{99m}$Tc, $^{94m}$Tc, $^{11}$C, $^{13}$N, $^{15}$O, and $^{76}$Br. In the case of being complexed with non-radioactive metals such as manganese, iron, and gadolinium, the same chelates are useful for MRI when used with nanoparticles or antibodies of the present invention. Macrocyclic chelates, such as NOTA, DOTA, and TETA, are used with types of metal and radiometals, preferably radionuclides of gallium, yttrium, and copper, respectively. The metal-chelate complex may be prepared very stably by fitting the size of ring to the corresponding metal. According to the present invention, cyclic chelates, such as macrocyclic polyethers useful for stably binding nuclides such as $^{223}$Ra to RAIT, may be prepared.

An immunoconjugate is a conjugate of an antibody component with a therapeutic or diagnostic agent. The diagnostic agent includes a radioactive or non-radioactive label and a contrast agent (a contrast agent suitable for magnetic resonance imaging, computed tomography, or ultrasound), and the radioactive label may be a gamma-, beta-, alpha-, Auger electron-, or positron-emitting isotope.

In the present invention, the "immunomodulator" typically stimulates immune cells to proliferate or become activated in an immune response cascade, such as macrophages, B-cells, and/or T-cells. An example of an immunomodulator is a cytokine. As will be obvious to those of ordinary skill in the art, interleukin and interferon are cytokines that stimulate the activity of T-cells or other immune cells.

Deoxyribonucleic acid (DNA), ribonucleic acid (RNA), peptide nucleic acid (PNA), or locked nucleic acid (LNA) may be linked directly or via a linker to the Fc site-specific conjugating peptide of the present invention. Since the DNA, RNA, PNA, and LNA are polymers having properties of specifically binding to a material having a complementary sequence, the Fc site-specific conjugating peptide to which the DNA, RNA, PNA or LNA is linked may be used in gene screening, biosensors, and the like.

The Fc site-specific conjugating peptide to which the DNA, RNA, PNA or LNA is linked may be immobilized on a solid support to be used as a biochip, biosensor, immunodetection kit, or complementary self-addressable chip.

In the present invention, the linker may comprise a reactive functional group, an amino acid, and a self-cleaving spacer.

The linker of the present invention may be in a form that links a specific residue in the Fc site-specific conjugating peptide substituted with a photoreactive functional group, with a substance, and may have a reactive site with an electrophilic group that reacts with the nucleophilic residue (e.g., cysteine) present on the Fc site-specific conjugating peptide substituted with a photoreactive functional group. The linker may comprise for example, a reactive functional group, an amino acid, and a self-cleaving spacer that binds to the Fc site-specific conjugating peptide substituted with a photoreactive functional group.

The functional group may be i) a maleimide group, an acetamide group, or derivatives thereof, ii) an aziridine group, an aryl halide, an acryloyl group, or derivatives thereof, or iii) an alkylating reactive group, an arylating reactive group, pyridyl disulfide, thionitrobenzoic acid, or derivatives thereof. Specifically, the linker may be in the form of: i) a maleimide group or derivative thereof-valine-citrulline-para-aniline benzoic acid (PABA); or ii) an acetamide group or derivative thereof-valine-citrulline-para-aniline benzoic acid (PABA), but the present invention is not limited thereto.

Binding of the Fc site-specific conjugating peptide substituted with a photoreactive functional group to the substance via the linker may be performed using a known method, for example, alkylation, disulfide exchange, or transthioesterification reaction. This enables conjugation of the conjugating peptide and the substance via a thiol group in the cysteine residue in the Fc site-specific conjugating peptide substituted with a photoreactive functional group.

In one embodiment, in the case of maleimide groups used for thiol-linker linkages, the nucleophilic reactivity of the thiol of the cysteine residue to the meleimide group is about 1,000 times greater than that of other amino acid functional groups present in proteins, e.g., amino groups or N-terminal amino groups of the lysine residue, and thus such maleimide groups may be used to specifically bind to cysteine. Thus, it can be seen that a substance modified with the conjugating peptide through a maleimide group or a derivative thereof or an acetamide group or a derivative thereof, for example, a bromo acetamide group or an iodo acetamide group, is linked to the Fc site-specific conjugating peptide substituted with a photoreactive functional group via a thioether bond of cysteine.

In another aspect, the present invention relates to a method of producing an antibody conjugate, comprising: (a) mixing a substance modified with the conjugating peptide with an Fc domain-containing molecule; (b) irradiating the mixture with light to induce a photoreaction and then to produce an antibody conjugate in which a photoreactive functional group of the substance modified with the conjugating peptide and the Fc domain-containing molecule are covalently linked; and (c) obtaining the produced antibody conjugate.

In the present invention, the light may be in a range from 320 nm to 380 nm, preferably 350 nm to 365 nm, but the present invention is not limited thereto.

In the present invention, "Fc domain-containing molecule" includes, without limitation, molecules containing an Fc domain that are specifically recognized by the Fc site-specific conjugating peptide and can be located adjacent thereto or can bind thereto. The Fc domain-containing molecule includes proteins, peptides, glycoproteins, glycopeptides, antibodies or fragments thereof, immunoglobulins or fragments thereof, and the like, which contain Fc domains. The antibodies and immunoglobulins are heterotetrameric glycoproteins of about 150 kDa, which include two identical light chains and two identical heavy chains. The fragments thereof containing an Fc domain may be fragments of antibodies or immunoglobulins treated with papain, from which light chains and heavy chains have been removed.

In the present invention, the Fc domain-containing molecule may be a targeted natural or non-natural antibody capable of specifically binding to a target molecule.

In the present invention, the antibody includes both polyclonal and monoclonal antibodies, as well as certain recombinant antibodies, such as chimeric, humanized or human antibodies. The antibodies may be receptor-specific antibodies or ligand-specific antibodies. In the present invention, the antibodies may also be receptor-specific antibodies that do not prevent ligand binding but prevent receptor activation. In addition, the antibodies may be therapeutic antibodies, antibodies that can bind to a separate therapeutic agent or diagnostic agent, antibodies for targeting that do not have therapeutic effects, or simply antibodies capable of performing an antigen-antibody reaction.

In the present invention, the antibody conjugate is a technology focused on a drug that particularly targets only specific tissue (e.g., cancer cells) by making the best use of advantages of antibodies, such as specificity, non-toxicity in circulation, and pharmacokinetics. Therefore, the antibody conjugate is also referred to as an immunoconjugate, and anticancer drugs for "targeted chemotherapeutics" fall within this range. The immunoconjugate consists of three components, including a drug, a monoclonal antibody, and a linker, which links the antibody and the drug. Particularly, for anticancer purposes, immunoconjugate technology is a method for delivering a substance having physiological activity to tumor cells using an antibody that specifically binds to a specific antigen expressed on the surfaces of cancer cells.

In one embodiment of the present invention, beta-lactamase (ß-lactamase (TEM-1)), beta-lactamase zymogen (Korean Patent Registration No. 1016956840000 (2017 Jan. 6)) and *Pseudomonas* exotoxin A (PE24) were used as substance compounds.

In the present invention, "ß-lactamase" (amino acid sequence of SEQ ID NO: 3) itself does not have cytotoxicity, but performs a mechanism for cleaving a prodrug having a beta-lactam ring to activate it as a drug, and thus, when co-treated with an appropriate prodrug, ß-lactamase may be used as an effective drug for treating tumors. In the present invention, an inactive prodrug called GC-mel may be used, and the β-lactam ring of GC-Mel is cleaved by β-lactamase, which is converted into a Melphalan form and alkylated to intracellular DNA, thereby inhibiting cell proliferation and causing cell apoptosis.

In the present invention, "ß-lactamase zymogen" (amino acid sequence of SEQ ID NO: 5) is expressed in an inactive state, in which beta-lactamase inhibitor protein (BLIP) is fused with ß-lactamase and expressed together. For example, however, a matrix metalloproteinase-2 (MMP-2) cleavage site, which is overexpressed in cancer cells, is introduced in a linker via which two proteins are linked, and thus BLIP is cleaved and removed in the vicinity of cancer cells, and consequently ß-lactamase exhibits activity; MMP-2 is overexpressed in cancer cells.

In the present invention, "PE24" (amino acid sequence of SEQ ID NO: 7) inactivates elongation factor-2 (EF-2) through ADP-ribosylation, which is involved in intracellular protein synthesis, thereby causing cell apoptosis (US Patent Registration No. 09388222 (2016 Jul. 12)).

In the present invention, the Fc domain-containing molecule may be selected from the group consisting of immunoglobulin-derived domains, combinations thereof, and Fc regions thereof. Preferably, the Fc domain-containing molecule may be selected from the group consisting of IgG, IgA, IgD, IgE, IgM, combinations thereof, and Fc regions thereof, and more preferably, may be IgG1 or an Fc region thereof, but the present invention is not limited thereto.

According to the present invention, in the obtaining of the produced antibody conjugate (process (c) above), since the Fc conjugating peptide binds to the Fc domain of a heavy chain of the antibody, when a photoreaction occurs between a fusion protein and the antibody, a total of three products (an unbound antibody, a form in which a substance modified with the Fc conjugating peptide is linked to the antibody, and a form in which two substances modified with the Fc conjugating peptide are linked to the antibody) may be obtained. In order to be used as a therapeutic drug, it is necessary to obtain a product having well-defined structures, and thus, one form must be isolated among the three reaction products. The antibody conjugate in which a substance modified with the Fc conjugating peptide is linked to the antibody has one binding site for the neonatal Fc receptor (FcRn) and can have a loner half-life time in circulation than the form in which two substances are linked the antibody masking the all two FcRn binding site.

The presence of unconjugated antibody may be prohibited under a reaction condition optimized for the substance and antibody concentrations, the ratio of the two reactants, the reaction temperature, the UV irradiation time, etc.

The antibody conjugates in which a substance modified with the Fc conjugating peptide is linked to an antibody and the antibody conjugate in which two substances modified with the Fc conjugating peptide are linked to the antibody may be separated from each other using the binding affinity between protein A and the Fc domain of the antibody. Protein A has a specific binding affinity to the $CH_2$—$CH_3$ domain interface of the Fc domain of the antibody, and thus is used as a resin for affinity chromatography, which is used for purification after the antibody is expressed. Thus, the antibody conjugate, in which two substances modified with the Fc conjugating peptide are linked to the antibody, does not bind to the protein A resin (W. L. DeLano et al, *Science*, 287(5456):1279-83, 2000). The form in which two substances are linked to the antibody may be removed through protein A affinity chromatography, and then anion chromatography may be further performed on the resultant product, thereby separating the unconjugated antibody and the form in which a substance modified with the Fc conjugating peptide is linked to the antibody due to the difference in the isoelectric point thereof.

In another aspect, the present invention relates to an antibody conjugate in which an antibody is covalently linked to a substance modified with the Fc conjugating peptide.

In another embodiment of the present invention, to confirm the activity of an IgG1-FcIII-PE24 conjugate, WST-8 assay and MTS assay were performed. In the WST-8 and MTS assays, a tetrazolium salt in a solution is changed into formazan by mitochondrial succinate dehydrogenase in media, which enables measurement at a specific absorbance, and thus cell viability can be confirmed through the absorbance measurement. A change in absorbance was measured by increasing the concentrations of the antibody conjugate within a specific range. As a result, it was observed that, as the concentration of the antibody conjugate in which the antibody and a substance modified with the Fc conjugating peptide were linked was increased, cell viability decreased. Thus, it was confirmed that the antibody conjugate of the present invention can be used as a therapeutic drug.

In the present invention, as an example of commercial human IgG, antibody conjugates were prepared using cetuximab or trastuzumab, and purified to confirm the activity thereof. Trastuzumab inhibits the activation of EGFR (EGF, TGFα) or HER4 (NRG1), which are dependent on ligands, by specifically acting on HER2, which forms a heterodimer with EGFR or HER4 and prevents downstream signaling. In addition, cetuximab inhibits the activation of EGFR, which is dependent on ligands (EGF, TGFα), and prevents downstream signaling.

Hereinafter, the present invention will be described in further detail with reference to the following examples. These examples are provided for illustrative purposes only, and it will be obvious to those of ordinary skill in the art that these examples should not be construed as limiting the scope of the present invention.

Example 1: Production of Fc Site-Specific Conjugating Peptide

To select a substitution position of p-benzoyl phenylalanine capable of performing efficient photoreaction binding, an Fc binding peptide variant in which the DNA nucleotide sequence at position 5, 10, or 11 in the amino acid sequence of SEQ ID NO: 1 was substituted with an amber codon was subjected to gene synthesis (Bioneer), followed by genetic manipulation so that the peptide can be expressed in the form of a fusion protein. The resulting peptide was expressed such that p-benzoyl phenylalanine is inserted at the amber codon position of the Fc binding peptide variants, and then purified. To observe a change in photoreaction efficiency according to the substitution position, human IgG1 and each of substances modified with the Fc binding peptide variant in which a DNA nucleotide sequence at position 5 of the above amino acid sequence is substituted with an amber codon (amino acid sequence of SEQ ID NO: 11, gene sequence of SEQ ID NO: 12), the Fc binding peptide variant in which a DNA nucleotide sequence at position 10 is substituted with an amber codon (amino acid sequence of SEQ ID NO: 13, gene sequence of SEQ ID NO: 14), and the Fc binding peptide variant in which a DNA nucleotide sequence at position 11 is substituted with an amber codon (amino acid sequence of SEQ ID NO: 15, gene sequence of SEQ ID NO: 16) were mixed in a ratio of 1:3 to thereby prepare samples, and then the samples were irradiated with ultraviolet light of 365 nm for 2 hours using a UV hand lamp (Lklab, U01-133-194) in a 1×PBS buffer (pH 7.4).

As a result, it was confirmed that the substance modified with the Fc binding peptide variant in which valine, which is the $10^{th}$ amino acid, is substituted with p-benzoyl phenylalanine exhibited the highest binding efficiency to the antibody (see FIG. 2). Accordingly, the sample, in which the position of valine (the $10^{th}$ amino acid) is substituted with p-benzoyl phenylalanine, exhibits the highest photoreaction efficiency, and the variant was names as 'Fc site-specific conjugating peptide.'

To construct a plasmid to express the Fc site-specific conjugating peptide, a peptide gene in which the $10^{th}$ amino acid is substituted with an amber codon was cleaved with NheI in a 2.1 NEB buffer and then with BamHI in a 3.1 NEB buffer. The buffer consisted of DDW, 10×NEB buffer 3.1, DNA, and a restriction enzyme and had a total volume of 50 μl, and treatment conditions were as follows: 37° C. for 4 hours. A pET21-a vector cleaved with the same restriction enzymes as described above to have both sticky ends and the cleaved peptide and plasmid genes were mixed in a molar ratio of 1:3 to a total volume of 10 μl, followed by ligation using T4 DNA ligase (NEB, England) at room temperature for 2 hours.

The ligated DNA mixed solution was mixed with 50 μl of E. coli DH10B (Thermo Scientific, C640003), which is a competent cell, to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the Fc site-specific conjugating peptide expression plasmid-1.

In addition, the same peptide gene in which the $10^{th}$ amino acid is substituted with an amber codon was cloned into pET22-b using NdeI and NcoI following the same procedure above, and the resulting plasmid was named as plasmid-2.

Example 2: Preparation of Substance Modified with Conjugating Peptide

Example 2-1: FcIII-ß-lactamase Cloning

As a template, a plasmid (pSPEL104) containing the entire sequence of ß-lactamase represented by SEQ ID NO: 4 was amplified through polymerase chain reaction (PCR) using primers shown in Table 1, and then cleaved with restriction enzymes BamHI and NotI and ligated to the Fc site-specific conjugating peptide expression plasmid-1.

PCR undergoes three stages of denaturation, annealing, and amplification, and the method is as follows. The reaction composition of PCR includes DDW, 10× pfu buffer, 0.2 mM dNTP, 20 pmol primers F/R, template, and 5 units Pfu polymerase, and the final reaction volume is 50 μl. After reacting at 95° C. for 2 minutes using BamhI-TEM1-f and TEM1-NotI-r of Table 1, the reaction product was subjected to 25 cycles of PCR, wherein the condition of one cycle was as follows: 95° C. for 30 seconds, 55° C. for 30 seconds, and 72° C. for 1 minute. After reaction completion, treated was performed at 72° C. for 10 minutes.

Table 1 shows PCR primers used in the present invention.

TABLE 1

| | |
|---|---|
| BamhI-TEM1-f | aaccttGGATCCggcggtggcagcgaaacgctggtgaaagtaaaagatg (SEQ ID NO: 24) |
| TEM1-NotI-r | AAGGTTgcggccgctTTAttaccaatgcttaatcagtga (SEQ ID NO: 25) |
| NdeI-FcIII V10*-f | AACCTTcatatgAAGAAAACAGCAATTGCTATTG (SEQ ID NO: 26) |
| FcIII V10*-NcoI-r | AAGGTTccatggTGTACACCActaTAATTCACC (SEQ ID NO: 27) |
| NcoI-β-lactamase zymogen-f | aaccttCCATGGggcggtATGGACGAGCGTAACCGTCAAA (SEQ ID NO: 28) |
| ß-lactamase zymogen-NotI-r | aaggttGCGGCCGCTttaTACAAGGTCCCACTGCCGCTTG (SEQ ID NO: 29) |

Cleavage was performed by treatment with the two restriction enzymes in a 3.1 NEB buffer. The buffer consisted of DDW, 10×NEB buffer 3.1, DNA, and a restriction enzyme and had a total volume of 50 μl, and treatment conditions were as follows: 37° C. for 4 hours. The Fc site-specific conjugating peptide expression plasmid-1 cleaved with the same restriction enzyme as described above to have both sticky ends and ß-lactamase were mixed in a molar ratio of 1:3 to a total volume of 10 μl, followed by ligation using T4 DNA ligase (NEB) at 25° C. for 2 hours.

Figure 3:
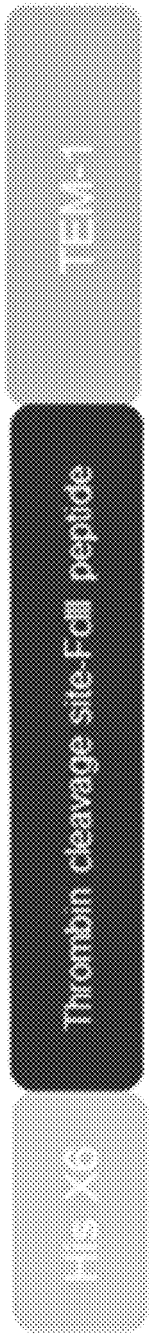
FIG. 3 is a schematic view illustrating a plasmid expressing ß-lactamase modified with the Fc conjugating peptide of the present invention (FcIII-ß-lactamase) and FcIII-ß-lactamase expressed in the plasmid.
Figure 3:
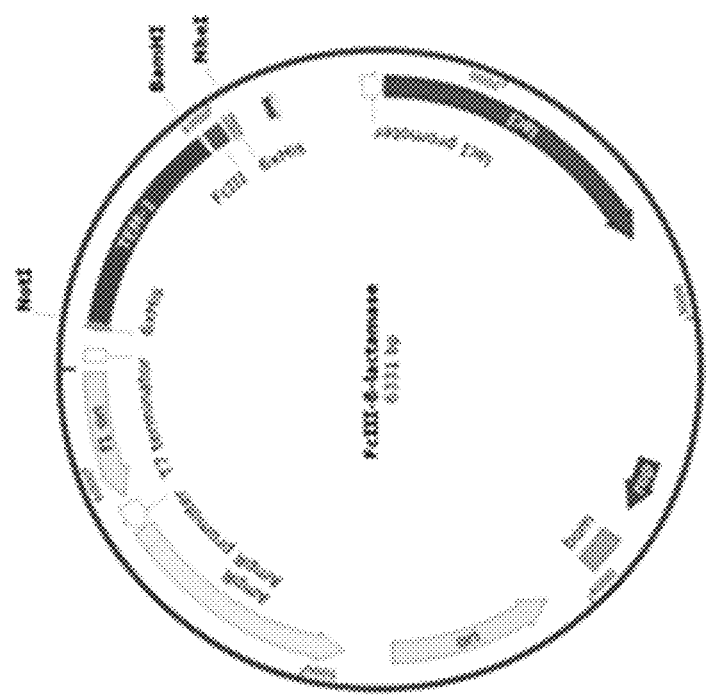

The ligated DNA mixed solution was mixed with 50 μl of E. coli DH10B (Thermo Scientific, C640003), which is a competent cell, to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the FcIII-ß- lactamase (amino acid sequence of SEQ ID NO: 17, gene sequence of SEQ ID NO: 18)-expressing plasmid (see FIG. 3).

Example 2-2: FcIII-ß-Lactamase Zymogen Cloning

As a template, a plasmid (pSPEL166) containing the 1-lactamase zymogen sequence (1353 bp) represented by SEQ ID NO: 6 was amplified through PCR using the primers of Table 1 under the same conditions as described above, and then cleaved with restriction enzymes NcoI and NotI, followed by ligation to the Fc site-specific conjugating peptide expression plasmid-2 in the same manner as described above.

Figure 4:
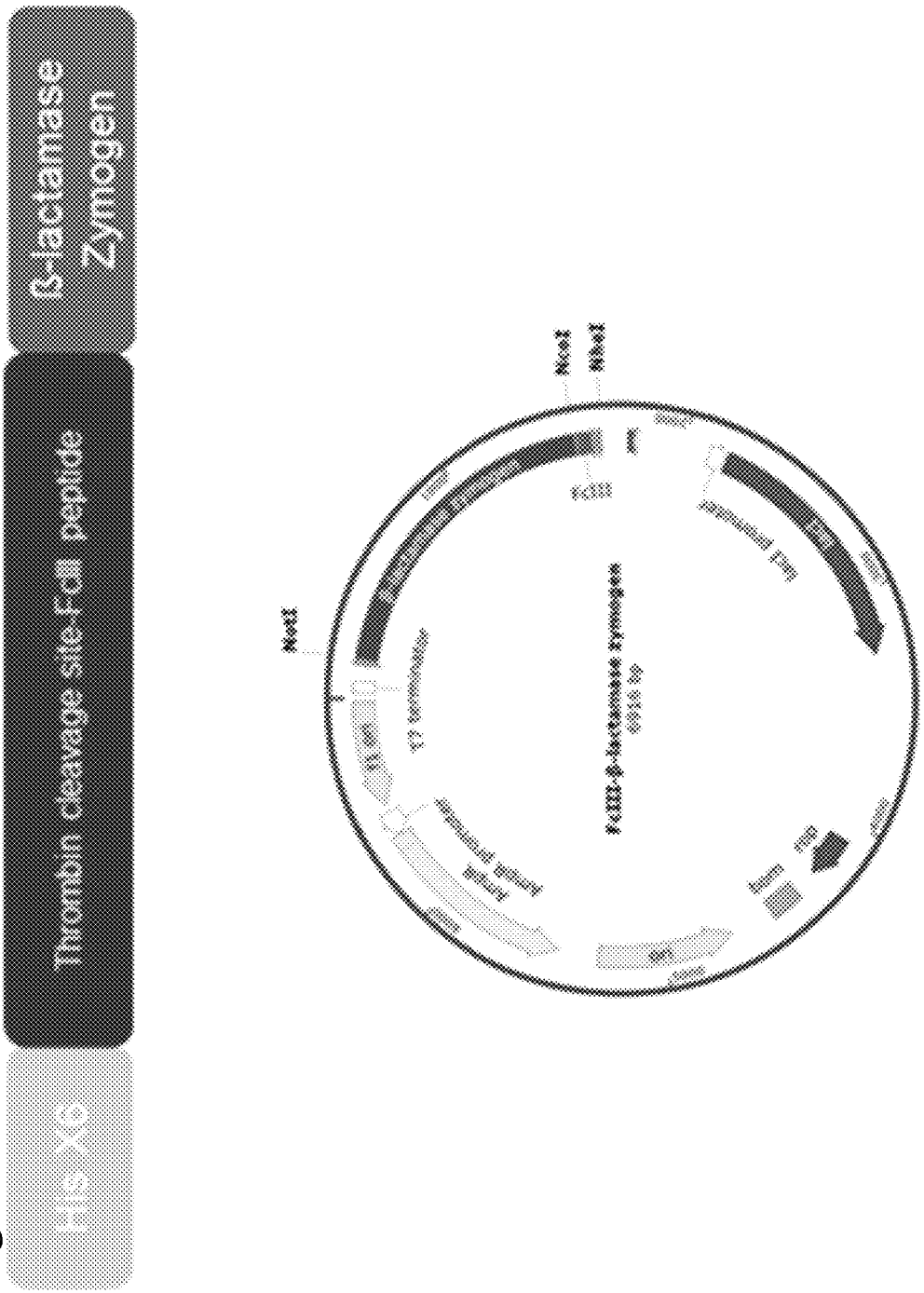
FIG. 4 is a schematic view illustrating a plasmid expressing ß-lactamase zymogen modified with the Fc conjugating peptide of the present invention (FcIII-ß-lactamase zymogen) and FcIII-ß-lactamase zymogen expressed in the plasmid.

The ligated DNA mixed solution was added to and mixed with 50 µl of *E. coli* DH10B (Thermo Scientific, C640003) to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the FcIII-8-lactamase zymogen (amino acid sequence of SEQ ID NO: 19, gene sequence of SEQ ID NO: 20)-expressing plasmid (see FIG. 4).

Example 2-3: FcIII-PE24 Cloning

Deimmunized PE24 represented by SEQ ID NO: 8 was obtained by gene synthesis (Bioneer), and then cleaved with restriction enzymes BamHI and NotI using the same method as that used above, followed by ligation to the Fc site-specific conjugating peptide expression plasmid-1.

Figure 5:
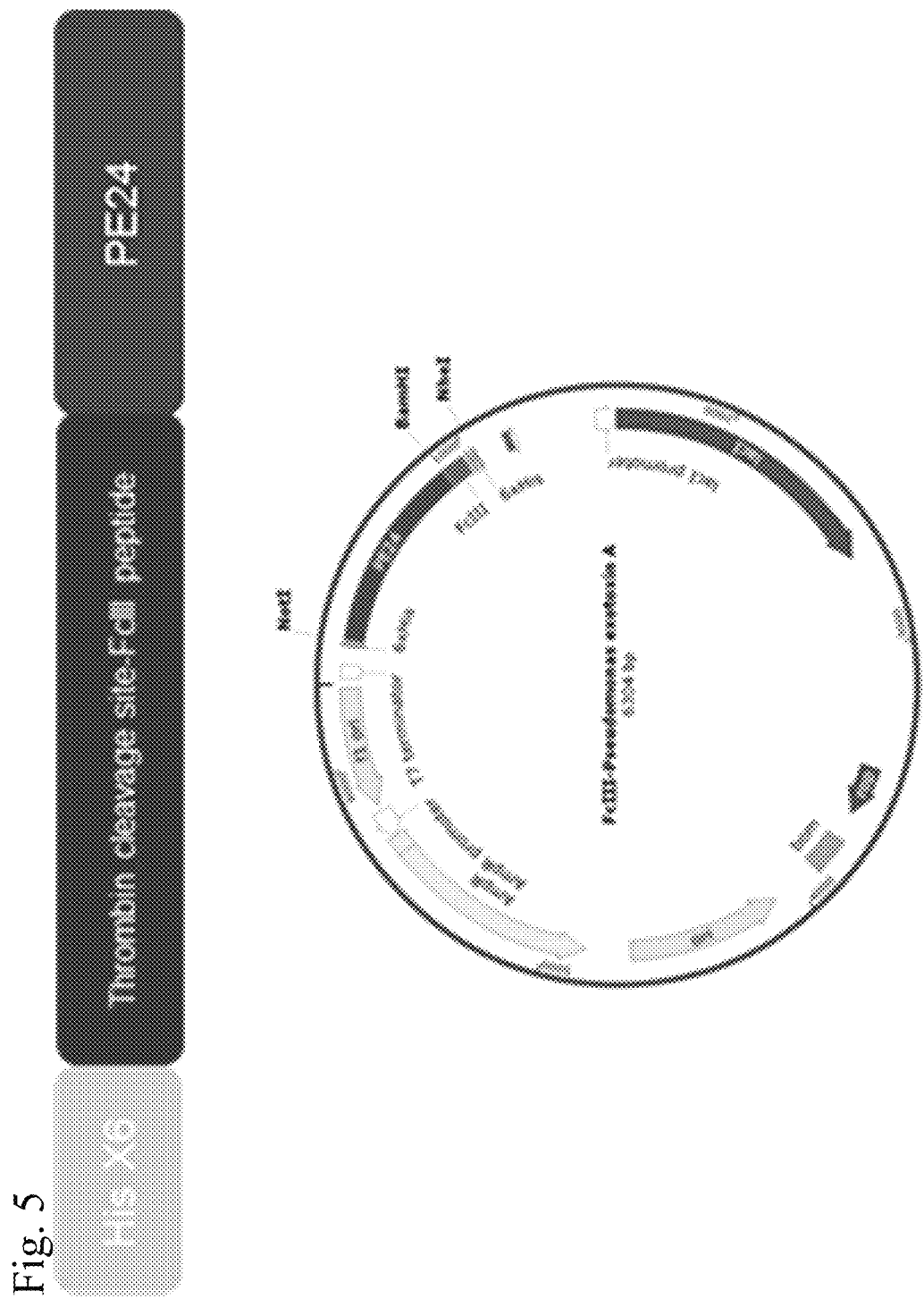
FIG. 5 is a schematic view illustrating a plasmid expressing PE24 modified with the Fc conjugating peptide of the present invention (FcIII-PE24) and FcIII-PE24 expressed in the plasmid.

The ligated DNA mixed solution was added to and mixed with 50 µl of *E. coli* DH10B (Thermo Scientific, C640003) to perform electroporation (Bio-Rad, USA). Subsequently, the mixture was spread on ampicillin-containing LB agar medium and cultured at 37° C. for 12 to 14 hours to obtain a transformed strain, followed by DNA prep (GeneAll, mini prep kit) to thereby obtain the FcIII-PE24 fusion protein (amino acid sequence of SEQ ID NO: 21, gene sequence of SEQ ID NO: 22)-expressing plasmid (see FIG. 5).

Example 2-4: Orthogonal TAG Codon Recognition tRNA and tRNA Synthetase Cloning

Figure 6A:
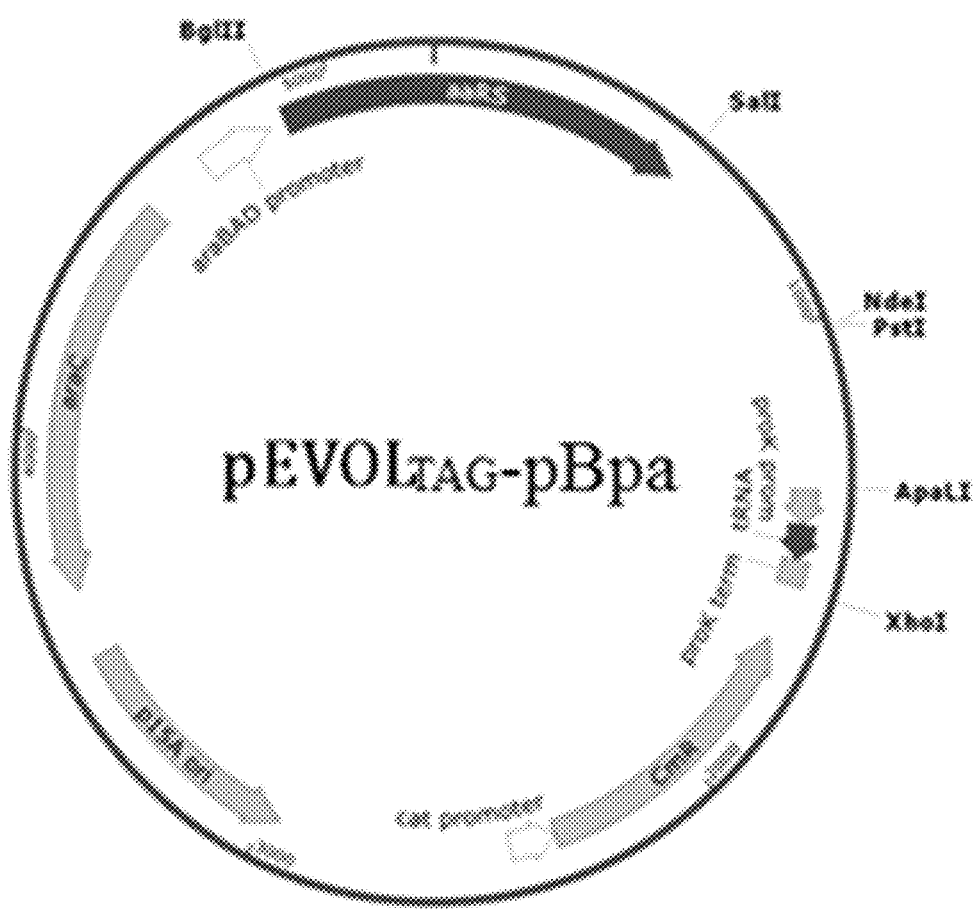
FIG. 6a illustrates a recombinant tRNA synthetase-expressing plasmid according to the present invention.

A p-benzoyl phenylalanine tRNA synthetase (amino acid sequence of SEQ ID NO: 9) sequence represented by SEQ ID NO: 10 was cleaved with SalI and BglII, and then ligated using, as a vector, a pEVOL plasmid including a tRNA sequence recognizing the TAG codon (Jason W. Chin et al, *PNAS vol.* 99, 11020-11024, 2002) (see FIG. 6a).

The ligated DNA mixed solution was added to and mixed with 50 µl of *E. coli* DH10B (Thermo Scientific, C640003) to perform electroporation (Bio-Rad, USA). Subsequently, the mixture was spread on chloramphenicol-containing LB agar medium and cultured at 37° C. for 12 to 14 hours to obtain a transformed strain, followed by DNA prep (Gene-All, mini prep kit) to thereby obtain the plasmid expressing tRNA synthetase (gene sequence of SEQ ID NO: 23) that inserts p-benzoyl phenylalanine by recognizing the TAG codon.

Figure 6B:
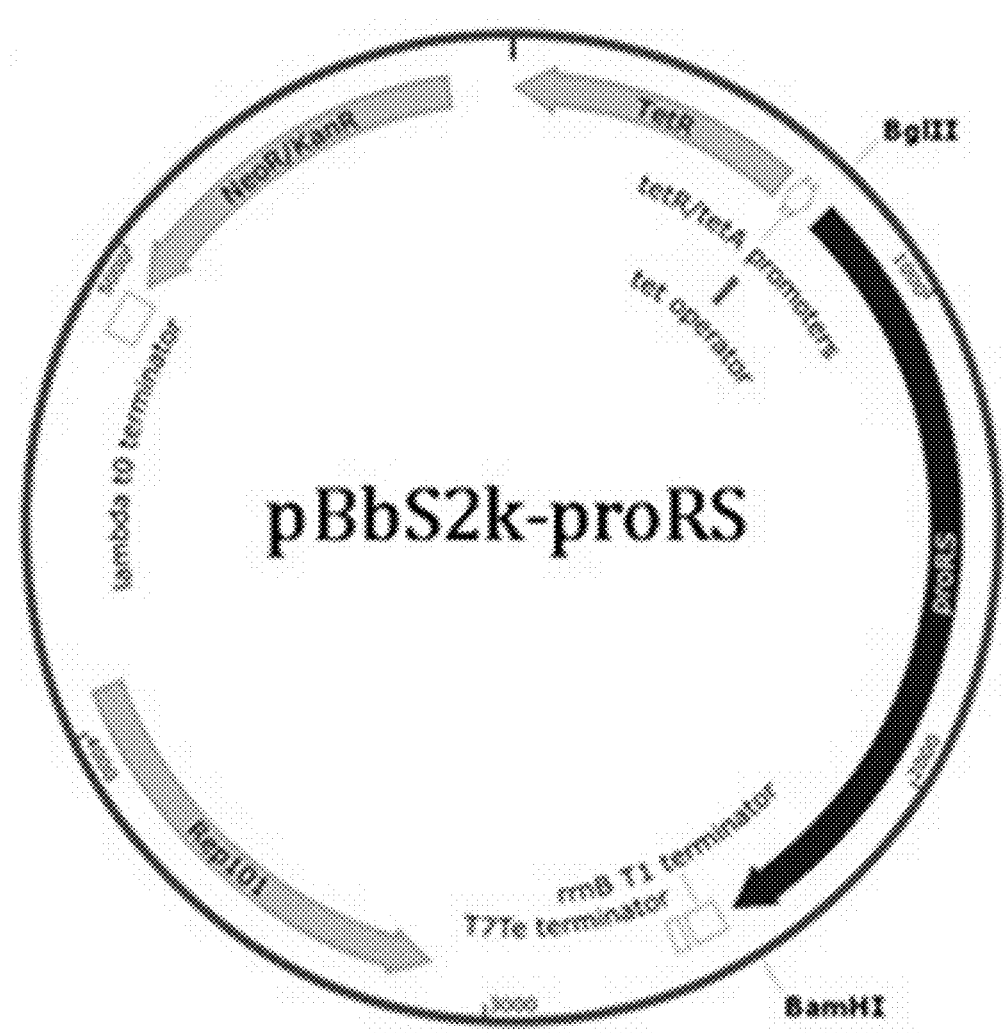
FIG. 6b illustrates a proline tRNA synthetase-expressing plasmid.

In the present invention, a pBbS2K plasmid containing a proline tRNA synthetase sequence was used (Byeong Sung Lee et al, *Biochimica Biophysica Acta*, S0304-4165, 2017) (see FIG. 6b).

Example 3: Expression and Purification of Substance Modified with Conjugating Peptide Example 3-1: Expression and Purification of FcIII-ß-Lactamase For the expression of FcIII-8-lactamase, the FcIII-ß-lactamase-expressing plasmid, the plasmid containing a pair of TAG codon recognition tRNA and p-benzoyl phenylalanine tRNA synthetase, and the plasmid containing proline tRNA synthetase were subjected to electroporation into *E. coli* BL21 (DE3) (SIGMA Aldrich, CMC0016), and then the resulting mixture was spread on an LB plate containing ampicillin, chloramphenicol, and kanamycin to thereby obtain a transformed strain.

The obtained single colony as a seed was seed-cultured at 37° C. and 180 rpm for 12 hours, and inoculated again in a medium in a ratio of 10:1, followed by incubation at 37° C. and 180 rpm for 6 hours. 200 ml of a 2×YT (containing ampicillin, chloramphenicol, and kanamycin) was inoculated with the culture solution in a ratio of 100:1, and then incubated at 37° C. and 180 rpm, and when the absorbance at 600 nm reached 0.5, arabinose was added to a final concentration of 0.2%, and anhydrotetracycline (aTc) was added thereto to 20 nM. When the absorbance reached 1.0, p-benzoyl phenylalanine 1 mM and isopropyl-β-D-thiogalactoside (IPTG) 1 mM were added as a final concentration, followed by incubation at 37° C. and 180 rpm over 12 hours.

To purify the expressed FcIII-8-lactamase, centrifugation was performed at 4° C. and 9300 g for 15 minutes. Subsequently, the supernatant was removed, followed by resuspension in 5 ml of a lysis buffer (0.75 M sucrose, 0.1 Tris, pH 8.0), addition of 0.05 g/ml of lysozyme and 10 ml of 1 mM EDTA, and rotating at 4° C. for 20 minutes. Thereafter, 1 ml of 0.5 M $MgCl_2$ was added thereto, followed by rotating at 4° C. for 10 minutes and centrifugation at 4° C. and 9300 g for 15 minutes, and the supernatant was separated.

Thereafter, to purify a histidine-tagged protein, 1 ml of a 50% Ni-NTA Superflow resin (Clonetech, USA) slurry was added to 20 ml of the supernatant, and while rotating at 4° C. for 1 hour, FcIII-8-lactamase was allowed to bind to the resin. After loading the reaction solution on an empty column, washing was performed by loading 30 ml of a washing buffer (50 mM $NaPO_3$, 300 mM NaCl, 40 mM imidazole), and 5 ml of an elution buffer (50 mM $NaPO_3$, 300 mM NaCl, 300 mM imidazole) was loaded to elute 6×His-tag FcIII-S-lactamase.

Example 3-2: Expression and Purification of FcIII-8-Lactamase Zymogen

For the expression of FcIII-ß-lactamase zymogen, the FcIII-ß-lactamase zymogen-expressing plasmid, the plasmid containing a pair of TAG codon recognition tRNA and p-benzoyl phenylalanine tRNA synthetase, and the plasmid containing proline tRNA synthetase were subjected to electroporation into *E. coli* BL21 (DE3) (SIGMA Aldrich, CMC0016), followed by culture in the same manner as in the expression of FcIII-S-lactamase, thereby expressing FcIII-ß-lactamase zymogen.

Subsequently, purification was performed under the same conditions as those of the purification of FcIII-ß-lactamase, to elute 6×His-tag FcIII-ß-lactamase zymogen.

Example 3-3: Expression and Purification of FcIII-PE24

For the expression of FcIII-PE24, the FcIII-PE24-expressing plasmid, the plasmid containing a pair of TAG codon recognition tRNA and p-benzoyl phenylalanine tRNA synthetase, and the plasmid containing proline tRNA synthetase were subjected to electroporation into E. coli BL21 (DE3) (SIGMA Aldrich, CMC0016), followed by culture in the same manner as in the expression of FcIII-ß-lactamase, thereby expressing FcIII-PE24.

Subsequently, purification was performed under the same conditions as those of the purification of FcIII-ß-lactamase, to elute 6× His-tag FcIII-PE24.

Example 4: Binding of Cetuximab and Substances Modified with Conjugating Peptides, and Separation and Activity of Conjugates

Figure 7:
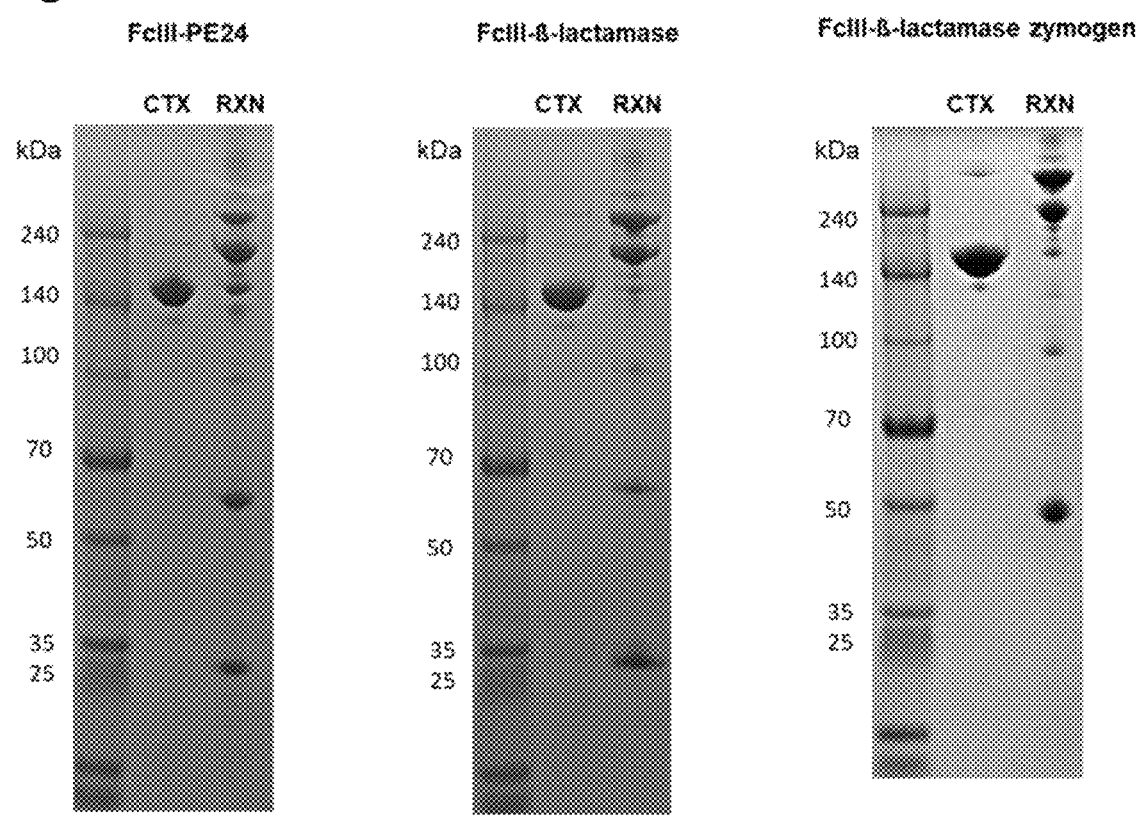
FIG. 7 illustrates the electrophoresis results of conjugating each of fusion proteins of the present invention and an antibody (cetuximab).

Example 4-1: Confirmation of Binding of Cetuximab and Substance Modified with Conjugating Peptide To confirm binding of an antibody and each of substances modified with the conjugating peptides obtained according to Example 3 (FcIII-8-lactamase, FcIII-8-lactamase zymogen, and FcIII-PE24), cetuximab and each of substances modified with the conjugating peptides were mixed in a ratio of 1:5, and irradiated with ultraviolet light of 365 nm for 2 hours using a UV hand lamp (Lklab, U01-133-194) on a pH 7.4 1×PBS buffer. As a result, it was confirmed that cetuximab was bound to each of the substances modified with the conjugating peptides (FcIII-8-lactamase, FcIII-ß-lactamase zymogen, and FcIII-PE24) (see FIG. 7).

To confirm whether each substance modified with the conjugating peptide accurately binds site-specifically to the $CH_2$—$CH_3$ domain interface of the antibody, 10 μM human IgG1 and 30 μM FcIII-8-lactamase were mixed in a fixed concentration ratio, and the mixture was treated with Z-domain while increasing the concentration thereof from 10-35 μM at intervals of 5 μM, and subjected to photoreaction while irradiated with ultraviolet light of 365 nm for 2 hours using a UV hand lamp. The Z-domain binds to the same $CH_2$—$CH_3$ domain interface as that of the FcIII peptide.

Figure 8:
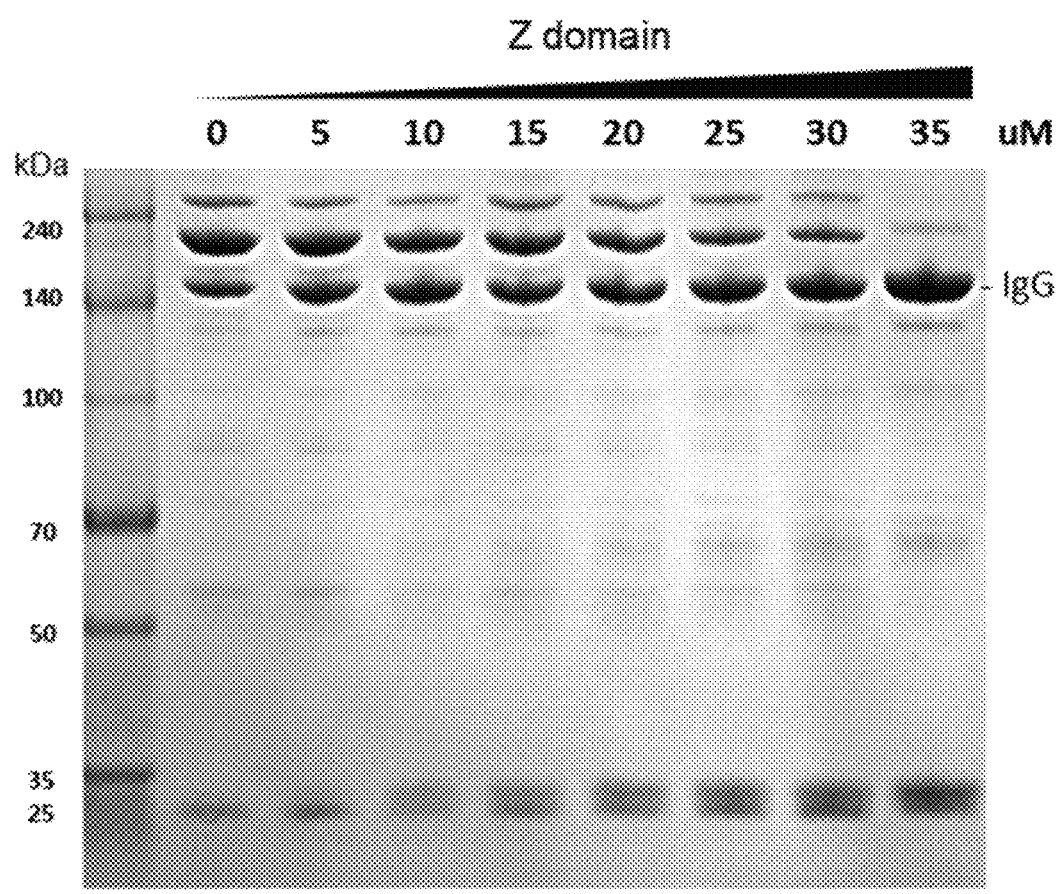

As a result, it was confirmed that the formed human IgG1-FcIII-8-lactamase was significantly reduced when photoreaction was performed after treatment with Z-domain at a concentration of 35 μM, which was higher than the concentration of FcIII-8-lactamase. It is suggested indirectly that the FcIII fusion protein binds site-specifically to the Fc domain of the antibody (see FIG. 8).

Figure 9A:
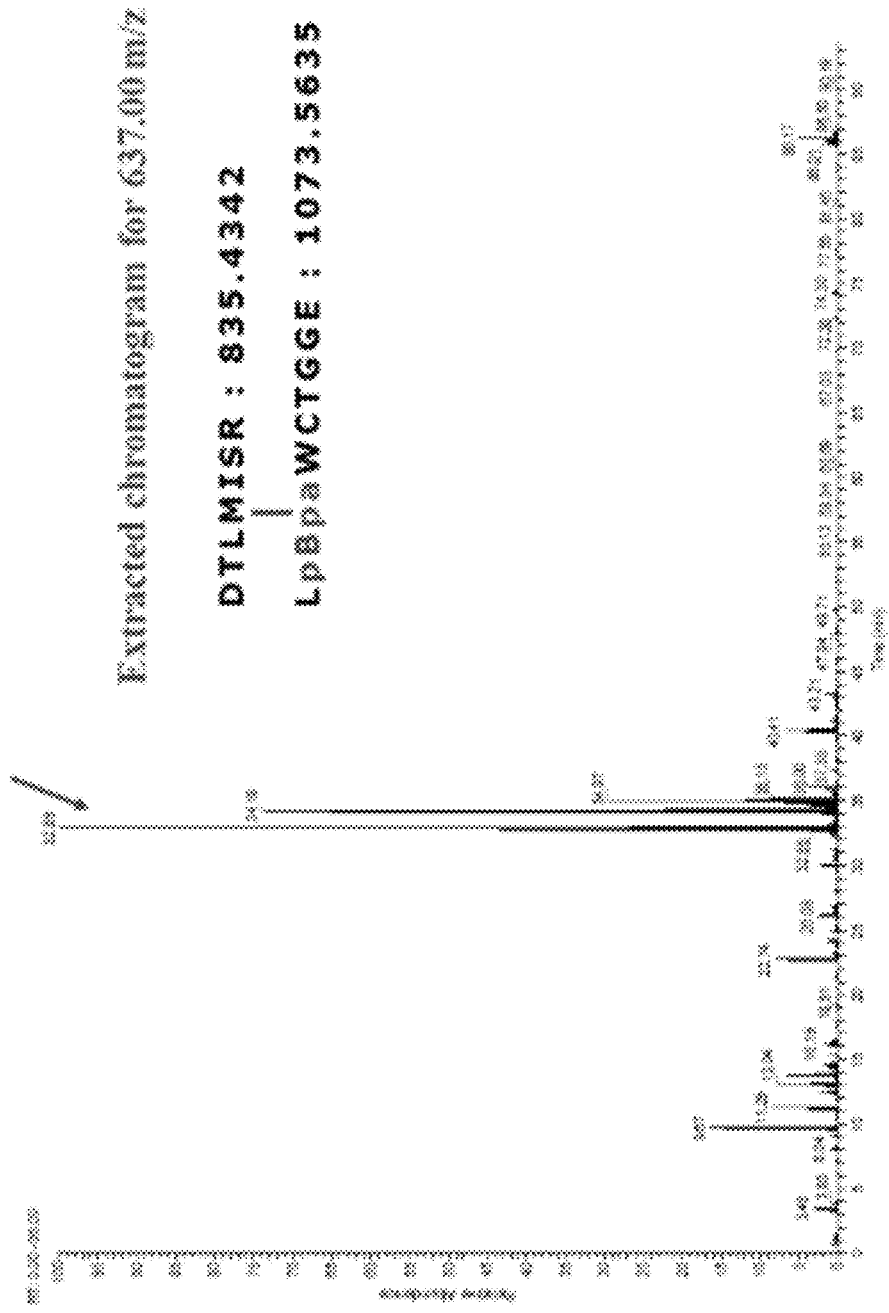
FIG. 9a-FIG. 9c illustrate the results of confirming, through LC-MS/MS, a site where the Fc conjugating peptide of the present invention and an antibody (cetuximab) were conjugated.
Figure 9B:
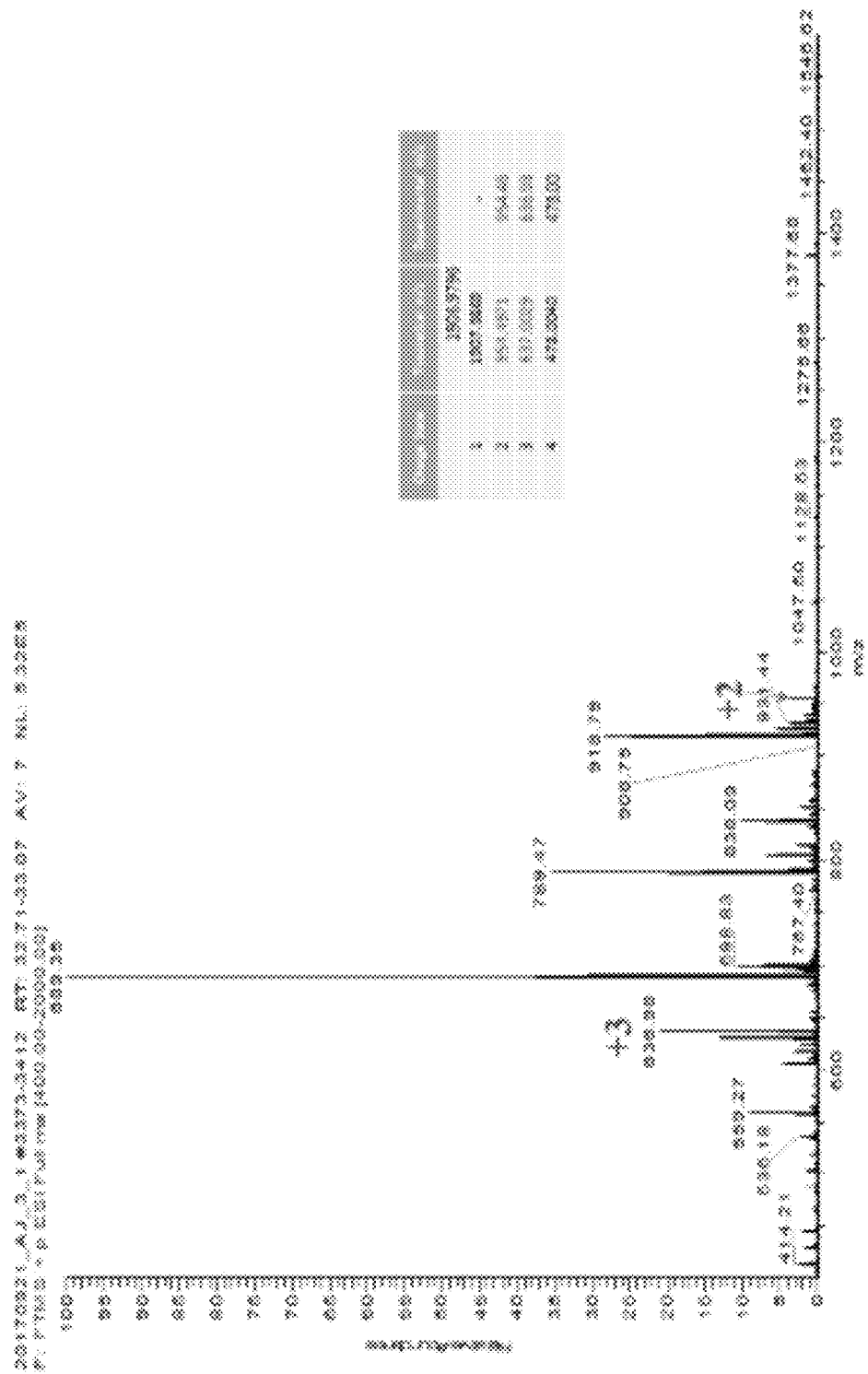
Figure 9C:
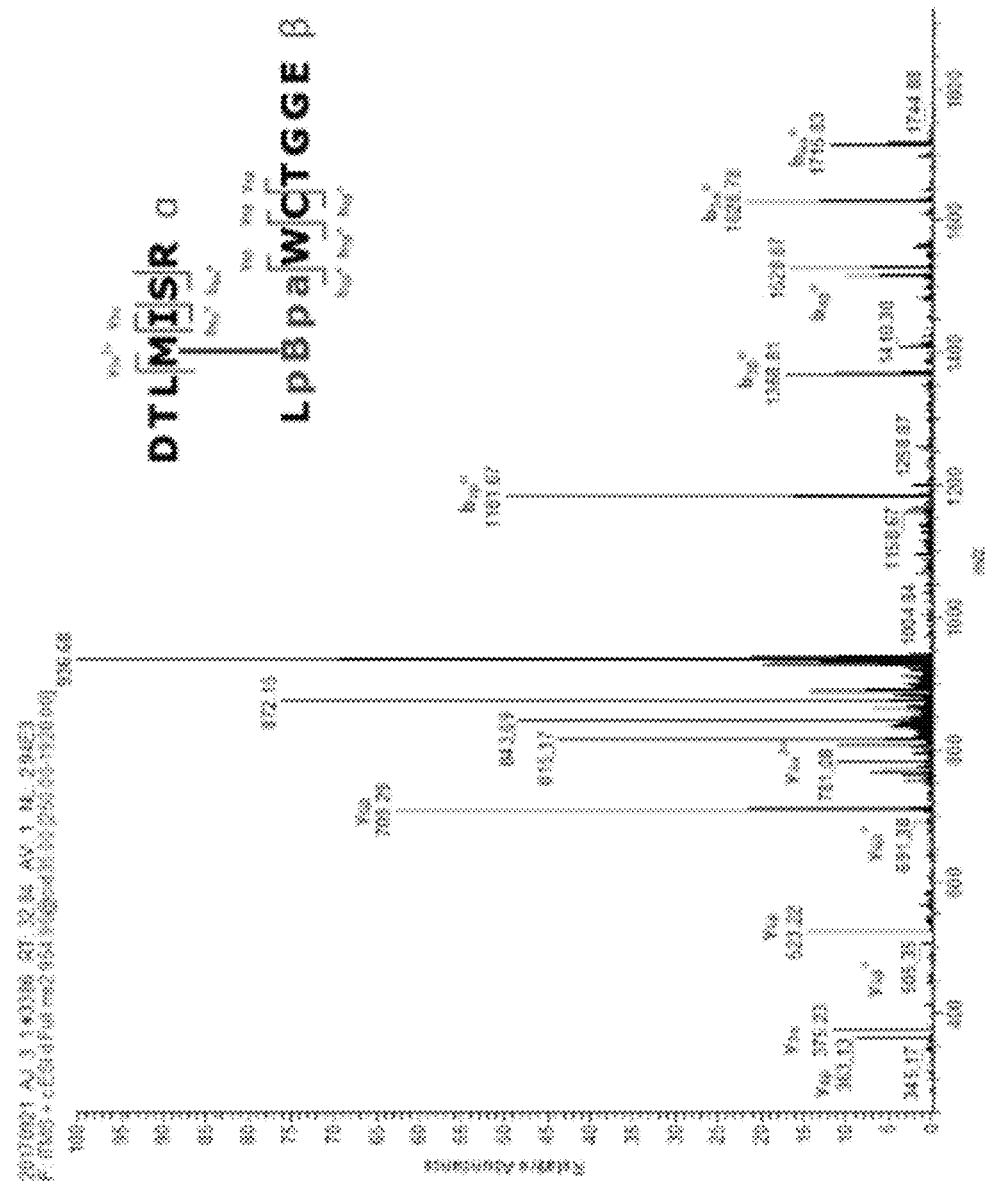

In addition, to confirm the conjugation position of the antibody and the substance modified with the conjugating peptide, analysis was performed using LC-MS/MS. The cetuximab-FcIII-S-lactamase conjugate was subjected to trypsin/glutamyl endopeptidase mixture digestion and analyzed. As a result, the peaks of conjugate fragments generated site-specifically were confirmed due to the covalent bond formed between the functional group of pBpa inserted at position Val10 of FcIII and the functional group of Met252 of the antibody (see FIG. 9).

Example 4-2: Separation of Antibody-Biomolecule Conjugate in which Cetuximab and Substance Modified with Conjugated Peptide are Bound To separate an antibody-biomolecule conjugate in which a substance modified with one conjugated peptide is bound to the antibody, an antibody-biomolecule conjugate in which the antibody is bound to the substance modified with the conjugating peptide of Example 4 was mixed with 5 ml of 1×PBS (pH 7.4), and then 1 ml of a protein A 50% resin slurry (CaptivA Protein A resin, Repligen) was added thereto, followed by rotating at 4° C. for 1.5 hours. The reaction solution was loaded on an empty column, allowing the resin to be completely precipitated, and washing was performed by loading 30 ml of 1×PBS (pH 7.4). Thereafter, 5 ml of an elution buffer (pH 3.0 0.1 M glycine) was loaded to obtain a product, and 125 μl of a neutralization buffer (pH 9.0 Tris) was added for pH titration.

Figure 10:
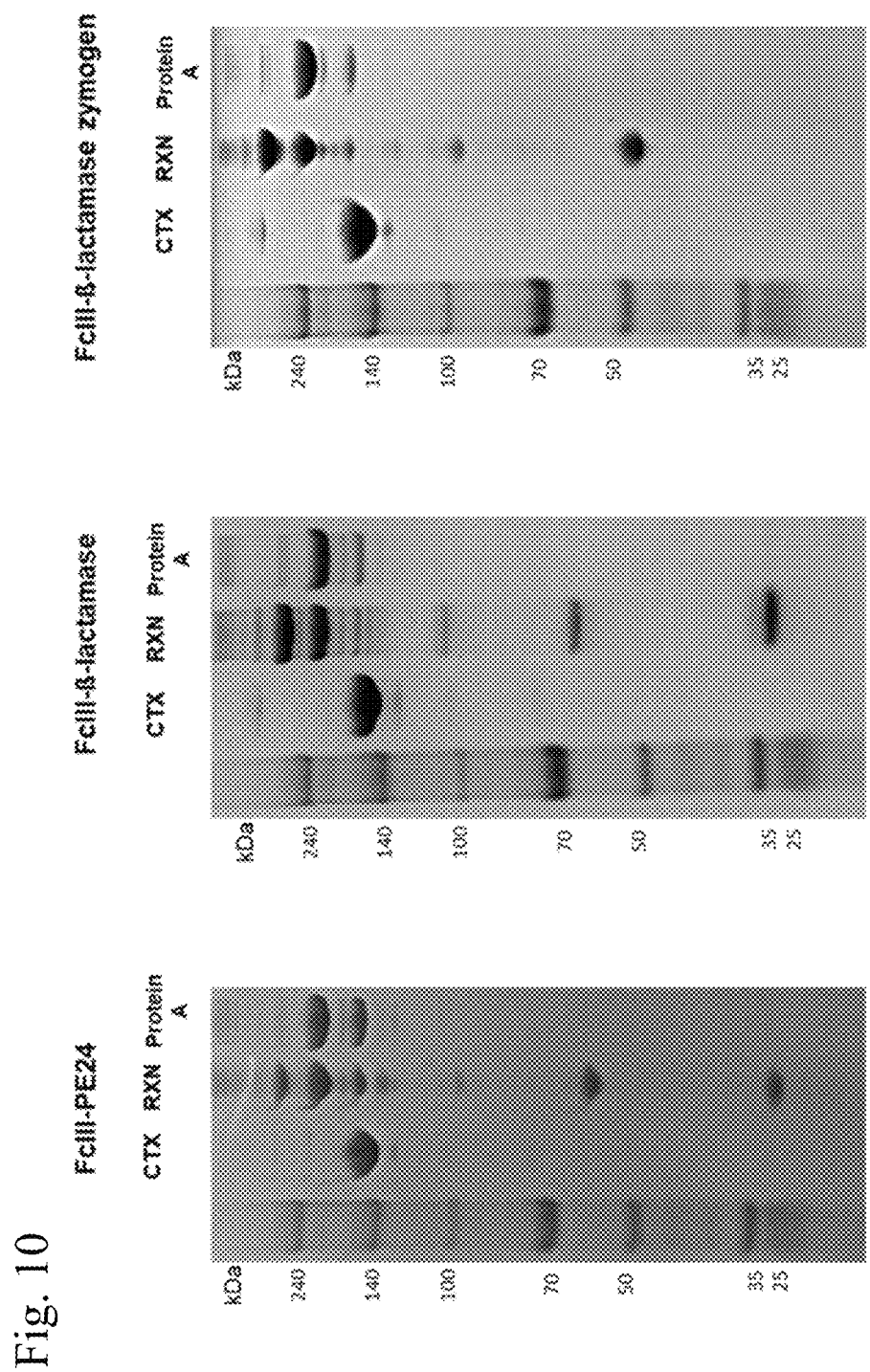
FIG. 10 illustrates the results of observing, through electrophoresis, isolation of a cetuximab-FcIII-PE24 conjugate in which the fusion protein of the present invention and an antibody (cetuximab) were conjugated at 1:1.

As a result, it was confirmed that the resulting product was a mixture of an unconjugated antibody and the antibody-biomolecule conjugate in which the substance modified with one conjugated peptide is bound to the antibody (see FIG. 10).

Example 4-3: Confirmation of EF2 Ribosylation Activity of Cetuximab-FcIII-PE24 Conjugate To measure the ADP-ribosylation activity of a cetuximab-FcIII-PE24 conjugate, ADP-ribose transition from biotinylated $NAD^+$ to EF-2 was measured using a method by Zhang and Snyder.

PE24 and the cetuximab-FcIII-PE24 conjugate were each diluted to 1 nM in 20 mM Tris-HCl (pH 7.4), 1 mM EDTA, and 1 mM DTT, respectively, and incubated with a wheat embryo extract in the presence of 50 nM biotinylated $NAD^+$ at 37° C. for 1 hour. Subsequently, the reaction was terminated with 5× sodium dodecyl sulfate (SDS) gel loading buffer. Proteins were separated on SDS-12% (w/v) polyacrylamide gel. Biotinylated EF-2 was detected by western blotting using a streptavidin-horseradish peroxidase (HRP) conjugate. Western blot images were analyzed using the ChemiDoc XRS system.

Figure 11:
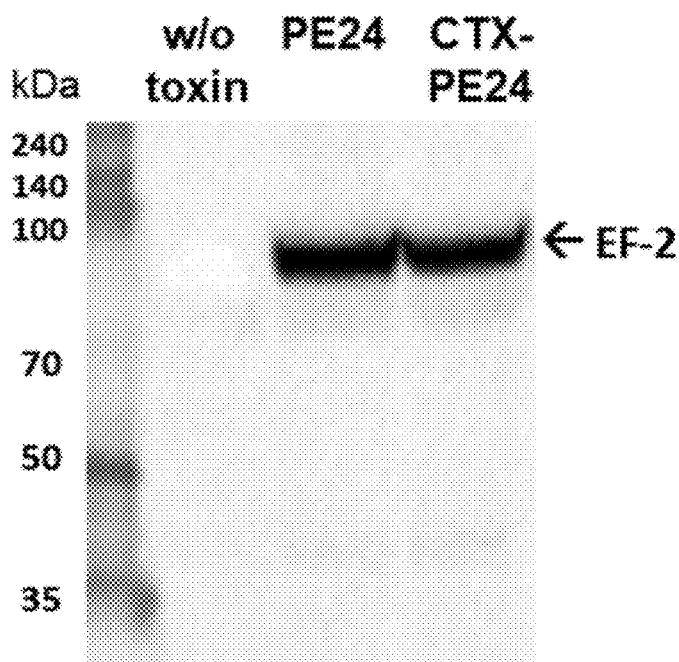
FIG. 11 illustrates the results of confirming the EF2 ribosylation activity of the cetuximab-FcIII-PE24 of the present invention.

As a result, it was confirmed that, like PE24, the cetuximab-FcIII-PE24 conjugate also inactivated EF-2 by ADP-ribosylation (see FIG. 11).

Example 4-4: Confirmation of Cell Growth Inhibitory Activity of Cetuximab-FcIII-PE24 Conjugate To confirm the activity of a cetuximab-FcIII-PE24 conjugate produced through photoreaction, cell viability assay was performed using a cell line overexpressing, on the cell surface, EGFR, which is a specific antigen to which cetuximab binds.

The EGFR cell line A431 (SIGMA Aldrich, 85090402) was cultured in a DMEM medium (10% FBS, streptomycin), and then seed-cultured on a 96-well plate at a density of $2\times10^3$ cells/well. After 24 hours, the cells were treated with cetuximab-FcIII-PE24 at concentrations of 0 nM, 0.016 nM, 0.16 nM, 1.6 nM, and 16 nM, and incubated at 37° C. and under the condition of 5% $CO_2$ for 72 hours. Thereafter, the cells were treated with 20 μl/well of an MTS solution (Promega, G3580), and after 2 hours, absorbance at 490 nm was measured.

Figure 12:
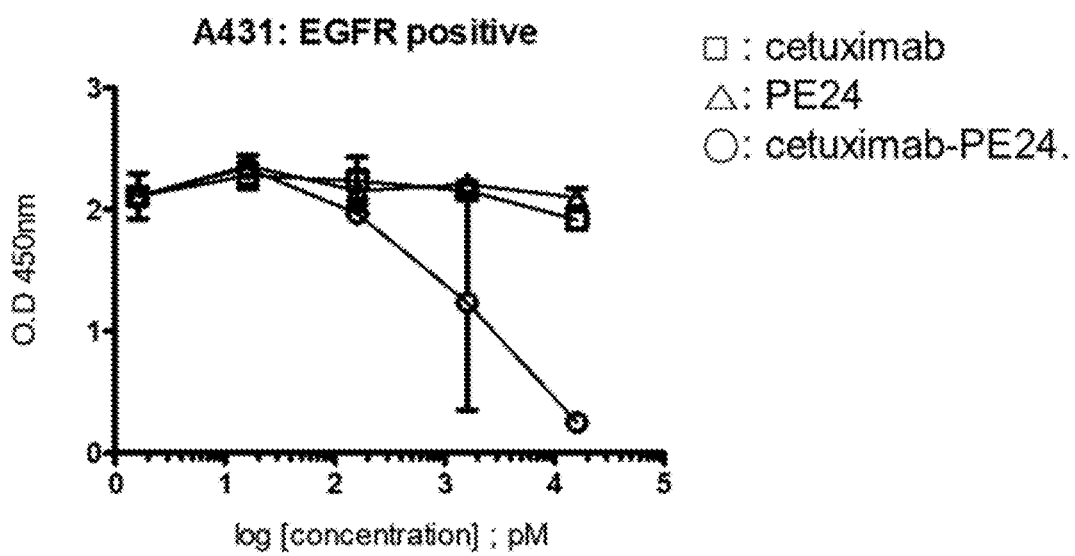
FIG. 12 illustrates the results of confirming the cell growth inhibitory activity of the cetuximab-FcIII-PE24 conjugate of the present invention.

As a result, it was confirmed that, the higher the concentration of cetuximab-FcIII-PE24 conjugate treated, the lower the absorbance, and cell viability was significantly reduced in the wells treated with the conjugate, compared to the wells treated with wild-type cetuximab and PE24 as negative controls (see FIG. 12).

Example 5: Binding of Trastuzumab and Substances Modified with Conjugating Peptides, and Separation and Activity of Conjugates

Example 5-1: Confirmation of Binding of Trastuzumab and FcIII-PE24

To confirm binding of an antibody and the substance modified with the conjugating peptide obtained according to Example 3 (FcIII-PE24), trastuzumab and PE24 modified with the conjugating peptide were mixed in a ratio of 1:5, and irradiated with ultraviolet light of 365 nm for 2 hours using a UV hand lamp (Lklab, U01-133-194) on a pH 7.4 1×PBS buffer. As a result, it was confirmed that trastuzumab and the substance modified with the conjugating peptide (FcIII-PE24) were bound (see FIG. 13).

Example 5-2: Separation of Trastuzumab-FcIII-PE24 Conjugate

To separate an antibody-biomolecule conjugate in which a substance modified with one conjugated peptide is bound to the antibody, an antibody-biomolecule conjugate in which the antibody is bound to the substance modified with the conjugating peptide of Example 4 was mixed with 5 ml of 1×PBS (pH 7.4), and then 1 ml of a protein A 50% resin slurry (CaptivA Protein A resin, Repligen) was added thereto, followed by rotating at 4° C. for 1.5 hours. The reaction solution was loaded on an empty column, allowing the resin to be completely precipitated, and washing was performed by loading 30 ml of 1×PBS (pH 7.4). Thereafter, 5 ml of an elution buffer (pH 3.0 0.1 M glycine) was loaded to obtain a product, and 125 μl of a neutralization buffer (pH 9.0 Tris) was added for pH titration.

Figure 13:
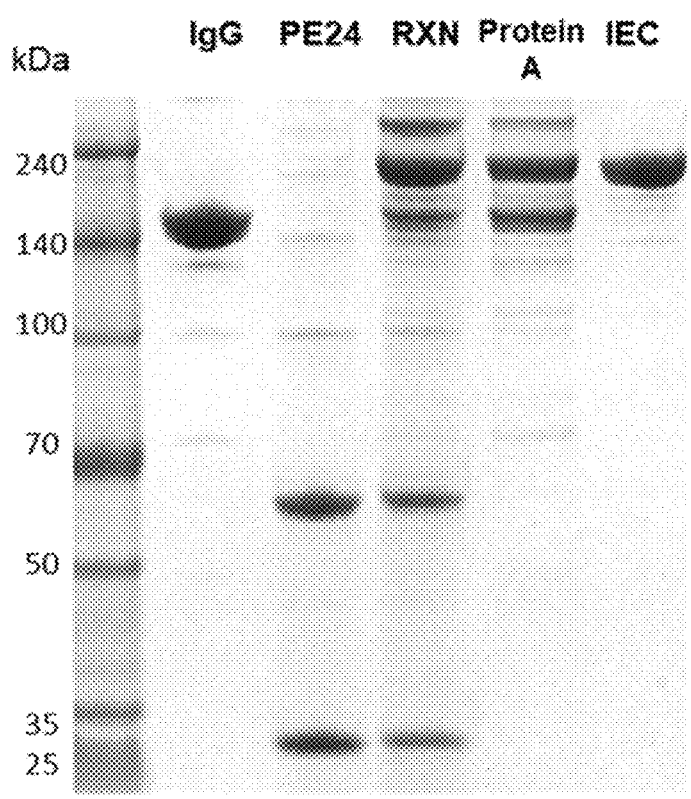
FIG. 13 illustrates the results of observing, by electrophoresis, site-specific conjugation between the fusion protein of the present invention and an antibody (trastuzumab) and isolation of a trastuzumab-FcIII-PE24 conjugate in which the fusion protein and the antibody were bound at 1:1.

As a result, it was confirmed that the resulting product was a mixture of an unconjugated antibody and the antibody-biomolecule conjugate in which the substance modified with one conjugated/peptide is bound to the antibody (see FIG. 13). The resulting product was mixed with a 20 mM phosphate buffer (pH 7.9), followed by continuous anion chromatography (mono-Q column, GE Healthcare Life Science, USA), thereby separating the unbound antibody and the form in which the substance modified with one conjugating peptide is bound to the antibody (see FIG. 13).

Example 5-3: Confirmation of Cell Growth Inhibitory Activity of Trastuzumab-FcIII-PE24 Conjugate To confirm the activity of a trastuzumab-FcIII-PE24 conjugate produced through photoreaction, cell viability assay was performed using cell lines overexpressing HER2, which is a specific antigen to which trastuzumab binds, and cell lines that do not express HER2.

HER2-overexpressing cell lines BT-474 (Korean Cell Line Bank, 60062), HCC-1954 (Korean Cell Line Bank, 951954), and MDA-MB-453 (Korean Cell Line Bank, 30131), and HER2 non-expressing cell line MDA-MB-231 (Korean Cell Line Bank, 30026) were cultured in RPMI media (10% FBS, streptomycin), and then seed-cultured in a 96-well plate at a density of $3-5\times10^3$ cells/well. After 24 hours, the cell lines were treated with trastuzumab-FcIII-PE24 at concentrations of 0 nM, 0.0064 nM, 0.032 nM, 0.16 nM, 0.8 nM, 4 nM, and 20 nM, and incubated at 37° C. and under the condition of 5% $CO_2$ for 72 hours. Thereafter, the cell lines were treated with 10 μl/well of a WST-8 solution (Dojindo, CK04-11), and after 2 hours, absorbance at 450 nm was measured.

Figure 14:
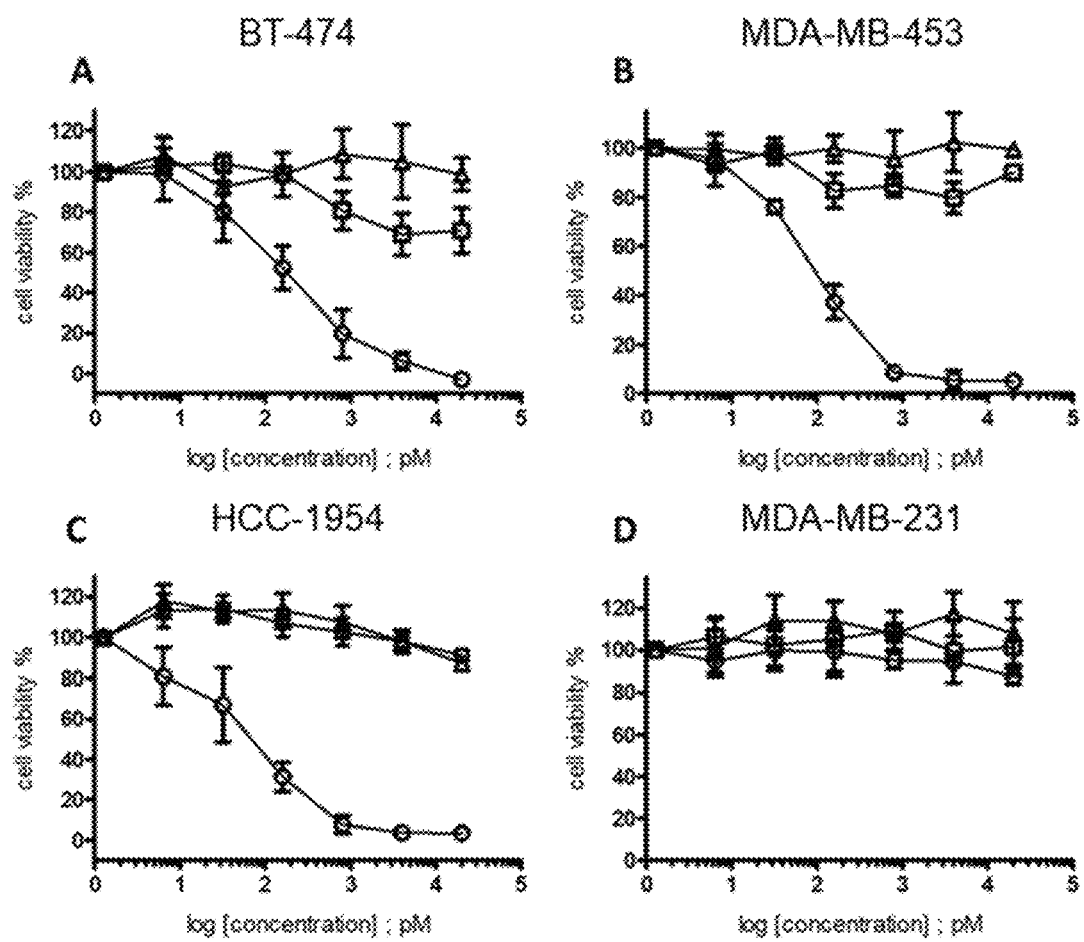
FIG. 14 illustrates the results of confirming the cell growth inhibitory activity of the trastuzumab-FcIII-PE24 conjugate of the present invention.

As a result, it was confirmed that, the higher the concentration of trastuzumab-FcIII-PE24 conjugate treated on the HER2-overexpressing cells, the lower the absorbance, and cell viability was significantly reduced in the wells treated with the conjugate, compared to the wells treated with wild-type trastuzumab and PE24 as negative controls. In contrast, it was confirmed that the cytotoxicity of the trastuzumab-FcIII-PE24 conjugate did not act on the HER2 non-expressing cells within the corresponding concentration range (see FIG. 14).

INDUSTRIAL APPLICABILITY

According to the present invention, by preparing a substance modified with the Fc site-specific conjugating peptide in which a specific position is substituted with a photoreactive functional group, and then conjugating an antibody to the substance through photoreaction, the substance can be linked site-specifically to the antibody with a high efficiency through simple photoreaction. Accordingly, the substance can be used for the production of antibody conjugates in which various types of substances and antibodies are linked, and commercialization thereof can be accelerated.

While specific embodiments of the present invention have been described in detail, it will be obvious to those of ordinary skill in the art that these detailed descriptions are merely exemplary embodiments and should not be construed as limiting the scope of the present invention. Therefore, the substantial scope of the present invention should be defined by the appended claims and equivalents thereof.

SEQUENCE LIST FREE TEXT

Electronic files attached.

---

The invention claimed is:

1. A substance modified with an Fc site-specific conjugating peptide mutant, wherein the substance is linked to the Fc site-specific conjugating peptide mutant either directly or via a linker,
wherein the Fc site-specific conjugating peptide mutant comprises the amino acid sequence of SEQ ID NO: 1, wherein the amino acid sequence of the Fc site-specific conjugating peptide further comprises a valine to p-benzoyl phenylalanine substitution at position 10, and wherein the Fc site-specific conjugating peptide mutant comprising p-benzoyl phenylalanine substitution at position 10 shows higher binding efficiency to Fc site of an antibody than a mutant comprising p-benzoyl phenylalanine substitution at position 5 or 11.

2. The substance according to claim 1, wherein the substance is a therapeutic agent or a diagnostic agent.

3. The substance according to claim 2, wherein the therapeutic agent or the diagnostic agent is selected from the group consisting of an enzyme, a hormone, a cytokine, an antibody, an antibody fragment, an analgesic, an antipyretic, an anti-inflammatory agent, an antibiotic, an anti-viral agent, an antifungal drug, a cardiovascular drug, a drug that acts on the central nervous system, a drug that affects renal function and electrolyte metabolism, and a chemotherapeutic agent.

4. The substance according to claim 1, wherein the linker comprises a reactive functional group, an amino acid, and a self-cleaving spacer.

5. A method of producing an antibody conjugate, wherein the method comprising:
(a) mixing a substance modified with the conjugating peptide according to claim 1 with an Fc domain-containing antibody;
(b) irradiating the mixture with light to produce an antibody conjugate in which the p-benzoyl phenylalanine and the Fc domain-containing molecule are covalently linked; and
(c) obtaining the produced antibody conjugate.

6. The method according to claim 5, wherein the light is in a range of 320 nm to 380 nm.

7. The method according to claim 5, wherein the Fc domain-containing antibody is a targeted natural or non-natural antibody capable of specifically binding to a target molecule.

8. The method according to claim 5, wherein the Fc domain-containing antibody is selected from the group consisting of IgG, IgA, IgD, IgE, IgM, combinations thereof, and Fc regions thereof.

9. The method according to claim 8, wherein the Fc domain-containing antibody is selected from the group consisting of IgG1-derived domain combinations and Fc regions thereof.

10. An antibody conjugate in which an antibody is linked to a substance modified with the conjugating peptide according to claim 1.

* * * * *